US007374756B2

(12) United States Patent
Aoki et al.

(10) Patent No.: US 7,374,756 B2
(45) Date of Patent: May 20, 2008

(54) SPECIFIC BINDING AGENTS FOR KSHV VIL-6 THAT NEUTRALIZE A BIOLOGICAL ACTIVITY

(75) Inventors: Yoshiyasu Aoki, Tokyo (JP); Giovanna Tosato, Bethesda, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 11/803,732

(22) Filed: May 14, 2007

(65) Prior Publication Data

US 2007/0243162 A1    Oct. 18, 2007

Related U.S. Application Data

(62) Division of application No. 11/493,687, filed on Jul. 25, 2006, now Pat. No. 7,235,365, which is a division of application No. 11/183,336, filed on Jul. 14, 2005, now Pat. No. 7,108,981, which is a division of application No. 10/333,121, filed as application No. PCT/US01/24179 on Jul. 31, 2001, now Pat. No. 6,939,547.

(60) Provisional application No. 60/221,719, filed on Jul. 31, 2000.

(51) Int. Cl.
*A61K 39/395*    (2006.01)

(52) U.S. Cl. .............. 424/130.1; 424/141.1; 435/345; 435/6

(58) Field of Classification Search .......... 435/6, 435/345; 424/130.1, 141.1
See application file for complete search history.

(56) References Cited

U.S. PATENT DOCUMENTS

| | | | |
|---|---|---|---|
| 5,801,042 A | 9/1998 | Chang et al. |
| 5,849,564 A | 12/1998 | Chang et al. |
| 5,854,398 A | 12/1998 | Chang et al. |
| 5,861,500 A | 1/1999 | Chang et al. |
| 5,948,676 A | 9/1999 | Chang et al. |

FOREIGN PATENT DOCUMENTS

| | | |
|---|---|---|
| WO | WO 98/03657 | 1/1998 |
| WO | WO 98/04576 | 2/1998 |

OTHER PUBLICATIONS

Hideshima et al., Characterization of signaling cascades triggered by human interleukin-6 versus Kaposi's sarcoma-associated herpes virus-encoded viral interleukin 6, *Clinical Cancer Research* 6:1180-1189 (2000).
Aoki et al., Angiogenesis and hematopoiesis induced by Kaposi's sarcoma-associated herpesvirus-encoded interleukin-6, *Blood* 93(12):4034-4043 (1999).
Aoki et al., Detection of viral interleukin-6 in Karposi's sarcoma-associated herpesvirus-linked diseases. *Blood* 94(10):431a (1999) (Abstract only).
Aoki et al., Indentification of unique binding site for gp130 in viral interleukin-6 encoded by human herpesvirus 8, *Blood* 96(11):572a (2000) (Abstract only).
Aoki et al., Detection of viral interleukin-6 in Kaposi sarcoma-associated herpesvirus-linked disorders, *Blood* 97(7):2173-2176 (2001).
Aoki et al., Serum viral interleukin-6 in AIDS-related multicentric Castleman disease. *Blood* 97(8):2526-2527 (2001).
Asou et al., Mechanisms of growth control of Kaposi's sarcoma-associated herpes virus-associated primary effusion lymphoma cells, *Blood* 91(7):2475-2481 (1998).
Brakenhoff et al., Development of a human interleukin-6 receptor antagonist, *Journal of Biological Chemistry* 369(1):86-93 (1994).
Burger et al., Human herpesvirus type 8 interleukin-6 homologue is functionally active on human myeloma cells, *Blood* 91(6):1858-1863 (1998).
Chow et al., Structure of an extracellular gp130 cytokine receptor signaling complex, *Science* 291:2150-2155 (2001).
Drexler et al., Constitutive cytokine production by primary effusion (body cavity-based) lymphoma-derived cell lines, *Leukemia* 13(4):634-640 (1999) (Abstract only).
Hoischen et al., Human herpes virus 8 interleukin-6 homologue triggers gp130 on neuronal and hematopoietic cells, *Eur. J. Biochem.* 267:3604-3612 (2000).
Jones et al., Involvement of interleukin-10 (IL-10) and viral IL-6 in the spontaneous growth of Kaposi's sarcoma herpesvirus-associated infected primary effusion lymphoma cells, *Blood* 94(8):2871-2879 (1999).
Molden et al., A Kaposi's sarcoma-associated herpesvirus-encoded cytokine homolog (vIL-6) activates signaling through the shared gp130 receptor subunit, *Journal of Biological Chemistry* 272(31) 19625-19631 (1997).
Moore et al., Molecular mimicry of human cytokine and cytokine response pathway genes by KSHV, *Science* 274(5293):1739-1744 (2000).

*Primary Examiner*—Ali R. Salimi
(74) *Attorney, Agent, or Firm*—Klarquist Sparkman, LLP

(57) ABSTRACT

A specific binding agent is provided, wherein the specific binding agent specifically binds Kaposi's sarcoma-associated herpesvirus (KSHV) interleukin-6 (vIL-6), and the specific binding agent neutralizes an activity of vIL-6. In one embodiment, the specific binding agent is an antibody. Methods are provided for using a specific binding agent that binds vIL-6, and neutralizes a biological activity of vIL-6. Methods of treatment for a KSHV-associated disorder are also provided. Methods for diagnosing a KSHV-associated disorder are provided, as are kits that include a specific binding agent of the invention. A method is also provided for testing an agent for effectiveness in treating a KSHV-associated disorder. The method includes incubating the agent with a cell free system comprising a vIL-6 receptor component and vIL-6, and comparing the binding of vIL-6 and the receptor component in the presence of the agent to binding of vIL-6 to the receptor component in the absence of the agent. A decrease in the binding of vIL-6 to the receptor component in the presence of the agent indicates that the agent is effective for treating the KSHV-associated disorder.

12 Claims, 11 Drawing Sheets

A

B

SPECIFIC BINDING AGENTS FOR KSHV VIL-6 THAT NEUTRALIZE A BIOLOGICAL ACTIVITY

PRIORITY CLAIM

This is a divisional of U.S. patent application Ser. No. 11/493,687 filed Jul. 25, 2006, now U.S. Pat. No. 7,235,365, which is a divisional of U.S. patent application Ser. No. 11/183,336 filed Jul. 14, 2005, issued as U.S. Pat. No. 7,108,981 on issued Sep. 19, 2006, which is a divisional of U.S. patent application Ser. No. 10/333,121 filed Jan. 14, 2003, issued as U.S. Pat. No. 6,939,547 on Sep. 6, 2005. U.S. patent application Ser. No. 10/333,121 is the § 371 U.S. national stage of PCT Application No. PCT/US01/24179 filed Jul. 31, 2001, which was published in English under PCT Article 21(2), and in turn claims the benefit of U.S. Provisional Application 60/221,719 filed Jul. 31, 2000. U.S. patent application Ser. Nos. 10/333,121, 11/183,336, and 11/493,687 are all incorporated by reference herein in their entirety.

FIELD OF THE INVENTION

This invention relates to the field of herpesviruses, more specifically to human herpesvirus 8 (HHV-8), also known as Kaposi's sarcoma associated herpesvirus (KSHV), and to agents that bind the viral IL-6 encoded by this virus.

BACKGROUND

Kaposi's sarcoma-associated herpesvirus (KSHV/HHV-8) is a newly described oncogenic herpesvirus originally identified in acquired immunodeficiency syndrome (AIDS)-associated Kaposi's sarcoma (KS) lesions (Chang et al., *Science* 266:1865, 1994). KSHV sequences are regularly detected in KS lesions from human immunodeficiency virus (HIV)-infected and non-infected individuals, primary effusion lymphoma (PEL), and a proportion of cases of Castleman's disease (Neipel et al., *J Virol* 71:4187, 1997; Schulz, *J Gen Virol* 79:1573, 1998). KSHV encodes various proteins that have features suggesting their role in promoting cellular growth and transformation, including viral homologues of cyclin D, G-protein coupled receptor, interferon regulatory factor, macrophage inflammatory proteins and IL-6. All these viral proteins display structural similarities to their cellular counterparts. KSHV viral IL-6 (vIL-6), encoded at open reading frame K2, has 24.8% amino acid sequence identity (49.7% similarity) to human IL-6 (hIL-6) and 24.2% identity (47.9% similarity) to murine IL-6 (mIL-6) (Moore et al., *Science* 274:1739, 1996; Neipel, et al., *J Virol* 71:839, 1997; Nicholas et al., *Nat Med* 3:287, 1997).

Cellular IL-6 acts on a wide variety of cell types, serving as a growth factor for myeloma, plasmacytoma and B cells, and promoting the terminal differentiation of B cells into Ig-secreting cells (Kishimoto et al., *Blood* 86:1243, 1995; Peters, et al., *Blood* 92:3495, 1998). This cytokine has been implicated in the pathogenesis of several diseases, including multiple myeloma and rheumatoid arthritis as well as KSHV-related diseases (Neipel et al., *J Virol* 71:4187, 1997). The IL-6 family of cytokines exerts its activities via receptor complexes that contain at least one subunit of the signal transducing protein gp130. The members of this family, which include IL-6, LIF, IL-11, oncostatin M (OSM), ciliary neurotrophic factor and cardiotrophin-1, are structurally related and exert many overlapping biological activities (Kishimoto et al., *Blood* 86:1243, 1995; Peters, et al., *Blood* 92:3495, 1998). Cell stimulation by any member of the IL-6 family of cytokines triggers homo- or hetero-dimerization of gp130. The dimerization of gp130 leads to activation of associated cytoplasmic tyrosine kinases and subsequent modification of transcription factors (Taga et al., *Annu Rev Immunol* 15:797, 1997). In addition to gp130, the high affinity, signaling receptor complexes for the IL-6-type cytokines contain at least one other receptor subunit. IL-6 utilizes a specific α-subunit (IL-6Rα), and the high affinity receptor-ligand complex consists of two molecules of each gp130, IL-6 and IL-6Rα (Hammacher et al., *J. Biol Chem* 273:22701, 1998). The formation of such hexameric receptor-complexes occurs in all situations in which the ligand requires a nonsignaling receptor for its association with gp130.

In spite of its limited sequence homology, vIL-6 displays many biological functions of cellular IL-6 (Aoki et al., *Blood* 93:4034, 1999). Studies in vitro and in vivo have shown that vIL-6 can stimulate the growth of KSHV-infected PEL cells (Jones et al., *Blood* 94:2871, 1999), promote hematopoiesis, act as an angiogenic factor by inducing vascular endothelial growth factor (Aoki et al., *Blood* 93:4034, 1999), and activate STAT1, STAT3 and JAK1 phosphorylation (Molden et al., *J Biol Chem* 272: 19625, 1997). The interactions of vIL-6 with the IL-6 receptor chains gp130/IL-6Rα have been studied both in human and murine cell culture systems (Nicholas et al., *Nat Med* 3:287, 1997; Molden, *J Biol Chem* 272:19625, 1997; Burger et al., *Blood* 91:1858, 1998; Wan et al., *J Virol* 73:8268, 1999; Gage et al., *AIDS* 13:1851, 1999), but v-IL-6 directed molecules that selectively interfere with this interaction have yet to be developed.

SUMMARY OF THE DISCLOSURE

A specific binding agent is provided, wherein the specific binding agent specifically binds Kaposi's sarcoma-associated herpesvirus (KSHV) interleukin-6 (vIL-6), and the specific binding agent neutralizes an activity of vIL-6. In one embodiment, the specific binding agent is an antibody.

Methods are provided for using a specific binding agent that binds vIL-6, and neutralizes a biological activity of vIL-6. For examples, methods for diagnosing a KSHV-associated disorder are provided, as are kits that include a specific binding agent of the invention.

In another embodiment, a method is provided for testing an agent for effectiveness in treating a KSHV-associated disorder. The method includes incubating the agent with a cell free system comprising vIL-6 and gp130, and comparing the binding of vIL-6 and gp130 in the presence of the agent to binding of vIL-6 to gp130 in the absence of the agent. A decrease in the binding of vIL-6 to gp130 in the presence of the agent indicates that the agent is effective for treating the KSHV-associated disorder.

BRIEF DESCRIPTION OF THE DRAWINGS

FIG. 3A displays the results obtained when SKW6.4 cells ($1\times10^4$ cells/well) were incubated in the presence of hIL-6 or MBPvIL-6 at various concentrations, and human IgM production in the supernatants was measured by human IgM ELISA. FIG. 3B displays the results obtained when SKW6.4 cells were incubated in the presence of MBPvIL-6 (2 µg/ml) and mAbs against vIL-6 (0 to 10 µg/ml). The results represent the means of triplicate cultures; error bars represent SDs. The asterisk (*) denotes the occurrence of a significant decrease in IgM secretion in cultures containing anti-vIL-6 mAbs p<0.0005), compared to cultures containing MBPvIL-6 (2 µg/ml) alone.

FIG. 6 A shows the detection of vIL-6 by a solid-phase sandwich ELISA using an anti-vIL-6 mouse monoclonal and a rabbit polyclonal antibodies. The lower limit of sensitivity (the minimum amount of protein detected with 95% confidence) was calculated at 43.8 pg/mL MBP-vIL-6, corresponding to approximately 14.7 pg/ml of vIL-6. The assay is linear (r=0.999) between 30 and 3,360 pg/ml of vIL-6.

hIL-6 is not recognized in this vIL-6 ELISA. FIG. 6B shows the detection of hIL-6, but not vIL-6, by a hIL-6-specific ELISA.

FIG. 9A is a scematic diagram showing vIL-6 ABCD four helix bundle connected by peptide loops. Site I, composed of the N-terminal region of the AB-loop and the C-terminal region of helix D, identifies the epitope recognized by the vIL-6 neutralizing antibodies described here, and corresponds to the presumed site where human IL-6 would interact with IL-6R. Site II on helix A and C, and site III on the initial part of the AB-loop and helix D represent binding surfaces to gp130. FIG. 9B is a schematic diagram of vIL-6 juxtaposed to gp130 in a tetrameric (2:2) signaling model based on the crystal structure of the complex.[22] vIL-6 site II is occupied by the D2D3 sites of one gp130 chain, and site III is occupied by the D1 site of another gp130 chain. Site I of vIL-6, comprising the outward helical face, is not occupied by gp130 and is sterically accessible for engagement by other molecules.

DETAILED DESCRIPTION OF THE SPECIFIC EMBODIMENTS

Figure 1:
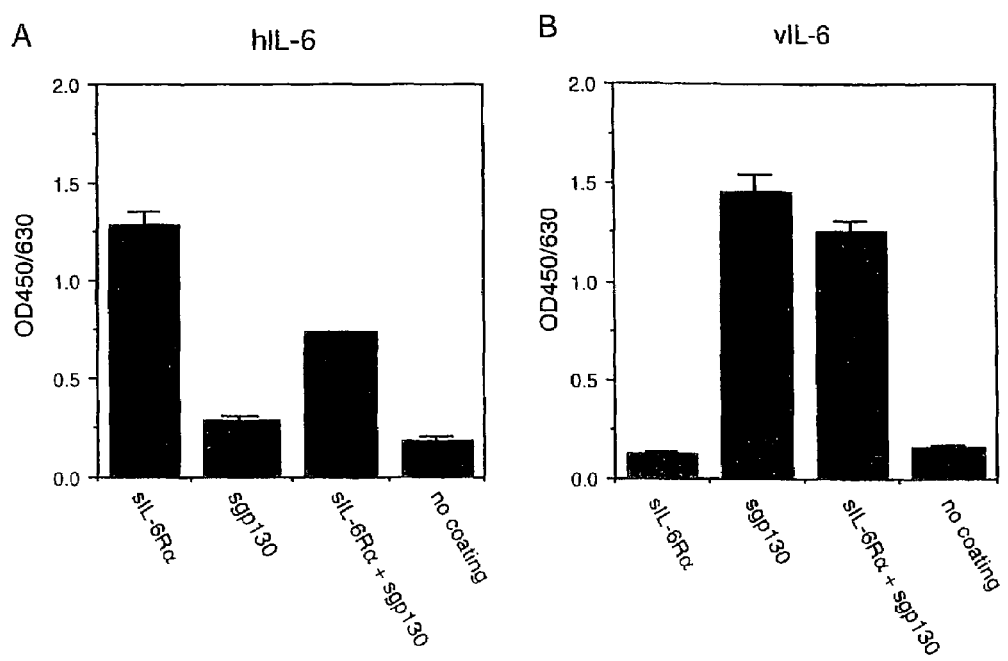
FIG. 1 is a bar graph demonstrating the binding of hIL-6 and vIL-6 to sIL-6R chains as detected by ELISA. Purified sIL-6Rα (5 µg/ml) and sgp130 (5 µg/ml) were immobilized on an ELISA plate and incubated with hIL-6 (50 ng/ml) or MBPvIL-6 (50 ng/ml). Bound protein was detected by rabbit anti-human or anti-viral IL-6 antibodies, followed by HRP-conjugated anti-rabbit IgG Abs. Panel A shows the results using bound protein detected with a rabbit polyclonal anti-hIL-6 antibody that recognizes hIL-6 but not vIL-6. Panel B shows the results using a polyclonal anti-MBPvIL-6 Ab which recognizes vIL-6 but not hIL-6. The results represent the means of triplicate assays; error bars represent SD. Representative data of three independent experiments are shown.

The following definitions and methods are provided to better define the present invention, and to guide those of ordinary skill in the art in the practice of the present invention. As used herein and in the appended claims, the singular forms "a", "an", and "the" include plural referents unless the context clearly dictates otherwise. Thus, for example, reference to "a cell" includes a plurality of such cells and reference to "the antibody" includes reference to one or more antibodies, and so forth.

Unless defined otherwise, all technical and scientific terms used herein have the same meaning as commonly understood to one of ordinary skill in the art to which this invention belongs.

Ameliorate: A lessening of the detrimental effect of the KSHV-associated disorder in a subject receiving therapy, such as a decrease in any parameter of the disease, including any symptoms of the disorder.

Complex (complexed): Two proteins, or fragments or derivatives thereof, are said to form a complex when they measurably associate with each other in a specific manner. Such association can be measured in any of various ways, both direct and indirect. Direct methods may include co-migration in non-denaturing fractionation conditions, for instance. Indirect measurements of association will depend on secondary effects caused by the association of the two proteins or protein domains. For instance, the formation of a complex between a protein and an antibody may be demonstrated by the antibody-specific inhibition of some function of the target protein. In the case of vIL-6, the formation of a complex between vIL-6 and a specific binding agent (e.g. a neutralizing antibody) for this protein can be measured by determining the degree to which the antibody inhibits an activity of vIL-6. Assays for vIL-6 activity are discussed further below.

Diagnostically effective: The amount of detectably labeled specific binding agent (e.g. a neutralizing antibody that binds vIL-6) that, when administered or utilized, is in sufficient quantity to enable detection of vIL-6.

ELISA: Enzyme-linked immunosorbent assay. A form of quantitative immunoassay based on the use of antibodies (or antigens) that are linked to an insoluble carrier surface, which is then used to capture the relevant antigen (or antibody) in the test solution. The antigen-antibody complex is then detected by measuring the activity of an appropriate enzyme that had previously been covalently attached to the antigen (or antibody).

Epitope: Any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Gp130: A transmembrane glycoprotein with a length of 918 amino acids, including an intracellular domain of 277 amino acids, that is a subunit constituent related to several cytokine receptors including the IL-6, IL-11, LIF, oncostatin M, CNTF cytokine receptors (see Gearing G P et al., *Science* 255: 1434-7, 1992; Hibi M. et al., *Cell* 63: 1149-57, 1990). Cytokines that share the gp130 subunits are sometimes referred to as the "IL-6 type family of cytokines." Gp130 is one component of the receptor that binds vIL-6.

Gp130 participates in the formation of high-affinity receptors for these cytokines by binding to low affinity receptor chains. Accordingly, gp130 has been called an "affinity converter." IL-6 binding to a cytokine receptor leads to the dimerization of gp130 and the activation/association of a family of tyrosine kinases (the Janus kinases) as the first step of intracellular signal transduction.

Using the structure of the growth hormone/growth hormone receptor complex as a paradigm for cytokine receptor complex assembly, IL-6-type cytokines are believed to have three topologically discrete sites of interactions with their receptors. Site I, if used, is always engaged by a non-signaling receptor: IL-6R, IL-11R or ciliary neurotrophic factor receptor. Site II is always engaged by gp130, and site III by a second signaling receptor gp130, OSMR or LIFR (Bravo et al., *EMBO J* 2000; 19:2399-2411). Within gp130, three binding epitopes have been identified as critical to its activation by human IL-6/IL-6R: one epitope involves the Ig-like domain (D1); another epitope is located in the cytokine binding module (D2D3); and the other is located in the membrane-proximal extracellular domains (D4D5D6) (Kurth et al., *J Immunol* 2000; 164:273-282).

IL-6: A cytokine produced by many different cell types (for review see Akira S. et al., *FASEBJ.* 4: 2860-7,1990; Wolvekamp and Marquet, *Immunology Let.* 24: 1-9, 1990). The main sources in vivo are stimulated monocytes, fibroblasts, and endothelial cells, although macrophages, T-cells and B-lymphocytes, granulocytes, smooth muscle cells, eosinophils, chondrocytes, osteoblasts, mast cells, glial cells, and keratinocytes also produce IL-6 after stimulation. Glioblastoma cells constitutively produce IL-6, and the factor can be detected also in the cerebrospinal fluid. Human milk also contains IL-6.

IL-6 is a protein of 185 amino acids glycosylated at positions 73 and 172. It is synthesized as a precursor protein of 212 amino acids. Monocytes express at least five different molecular forms of IL-6 with molecular masses of 21.5-28 kDa. The forms differ mainly by post-translational alterations such as glycosylation and phosphorylation. The human IL-6 gene has a length of approximately 5 kb and contains five exons. It maps to human chromosome 7p21-p14 between the markers D7S135 and D7S370.

The crystal structure of IL-6 has identified an antiparallel four helix bundle (A, B, C and D) with a topology common to a number of other cytokines in the superfamily (Somers et al., *EMBO J* 1997; 16:989-997). Extensive studies, including mutagenesis and mapping epitopes of function-blocking or activating Ab, have demonstrated that the contact points of human IL-6 with its receptor complex are mediated by three distinct sites named I, II and III (Brakenhoff et al., *J Immunol* 1990; 145:561-568; Savino et al., *EMBO J* 1994; 13:5863-5870; Savino et al., *EMBO J* 1994; 13:1357-1367; Kalai et al., *Blood* 1997; 89:1319-1333). Site I, formed by the C-terminal part of helix D and in part by the AB-loop, interacts with IL-6R Site II, formed by a limited number of exposed residues on helix A and helix C, and site III, formed by residues at the beginning of helix D spatially flanked by residues in the initial part of the AB-loop, bind to gp130. (Somers et al., *EMBO J* 1997; 16:989-997).

Many assays have been developed to detect IL-6 (e.g. see Anderson et al., *Kidney Internat,* 40: 1110-7, 1991; De Groote et al., *J. Immunol Meth.* 163: 259-67,1993; Guba et al., *Blood* 80: 1190-8,1992; Helle et al., *J. Immunol Meth.* 138: 47-56, 1991). For example, IL-6 can be detected in bioassays employing IL-6 responsive cell lines (e.g. 7TD1, B9, CESS, KPMM2, KT-3, M1, MH60-BSF-2, MO7E, Mono Mac 6, NFS-60, PIL-6, SKW6-C14, T1165, XG-1). IL-6 can be assayed also by its activity as a hybridoma growth factor. Immunoassays and/or colorimetric tests are also available for IL-6. An alternative and entirely different detection method is RT-PCR to detect IL-6 mRNA. In addition, an ELISA assay exists for detecting the receptor-associated gp130 protein.

Isolated: An "isolated" biological component (such as a nucleic acid molecule, protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Kaposi's Sarcoma-Associated Herpesvirus (KSHV): A unique herpesvirus (also known as human herpes virus 8 or HHV-8) which has been identified in 100% of amplifiable samples of Kaposi's sarcoma in AIDS patients (patients infected with human immunodeficiency virus (HIV)) as well as in HIV-negative patients. The virus can be isolated from PBMC as well as Kaposi' sarcoma tumor cells. HHV-8 also contains a considerable number of viral genes that are similar to cellular genes in an 'oncogenic cluster' within the virus genome. The genes in the oncogenic cluster are believed to be involved in the development of malignancy (See Boshoff, *Nature* 391: 24-25, 1998). In addition to Kaposi's sarcoma, this virus may play a role in the development of peripheral effusion lymphoma and a form of severe lymph node enlargement, called Castleman's disease.

In North America, probably less than 10% of the general population has been infected with KSHV. The rates of KSHV infection in the general population of Mediterranean countries (Italy, Greece, Israel, Saudi Arabia) are higher than in North America and Northern Europe. Adult populations in some portions of Africa have very high infection rates (>50%). It is believed that KSHV is transmitted by sexual and non-sexual routes. Over 95% of persons who are healthy and infected with KSHV do not have symptoms. However, symptoms occur once an infected individual is immunosuppressed, such as by the use of pharmaceutical immunosuppressants (e.g. as used in transplant patients or to treat autoimmune disease), as a result of an HIV infection, or from the use of chemotherapy. In addition, KSHV-related disease can also occur in persons without obvious immunodeficiency, but this is rare and primarily occurs among elderly men.

The viral genome (140 kb) of KSHV has been sequenced completely. The viral genome contains various open reading frames encoding proteins that mimic the actions of cytokines or that are involved in cytokine signaling.

KSHV-associated disorder: Any disorder associated with infection of a subject, such as a human subject, with KSHV. In one embodiment, the subject is also infected with a human immunodeficiency virus (HIV). In one specific, non-limiting example, the disorder is Kaposi's sarcoma. In another specific, non-limiting example, the disorder is Castleman's disease. In yet another specific, non-limiting example, the disorder is primary effusion lymphoma (PEL).

KSHV viral IL-6 (vIL-6): The region of the genome of KSHV termed ORF-K2 encodes a structural homologue of IL-6, termed viral IL-6 (vIL-6, see U.S. Pat. No. 5,861,500, herein incorporated by reference). The vIL-6 is homologous to cellular IL-6, and has a 62 percent amino acid similarity to human IL-6. The cysteine residues involved in disulfide bridging and the highly conserved region involved in receptor binding are retained in the viral gene product (see Burger, *Blood* 91:1858-1863,1998; Molden et al., *J. Biol. Chem.* 272: 19625-19631, 1997; Neipel et al., *J. Virol.* 71: 839-842, 1997). KSHV vIL-6 binds receptor components on the cell membrane. One of the receptor components that binds KSHV vIL-6 is gp130.

vIL-6 is functionally active and can substitute for human IL-6 in several assays. For example, vIL-6 prevents mouse myeloma cell apoptosis. It also supports proliferation of tumor cells dependent on exogenous IL-6 for growth and/or survival, such as the human myeloma cell line INA-6. vIL-6 is also functional in B9 proliferation bioassays. In addition, vIL-6 has been shown to activate the signaling pathways of cytokines involving STAT proteins and Janus kinases via interactions with the gp130 signal transducing subunit. This interaction is independent of the IL-6 receptor alpha chain and may influence disease pathogenesis upon KSHV infection by interfering with signaling through gp130 in response to native cytokines. vIL-6, as used herein, includes the amino acid sequence encoded by ORF-K2, conservative variants thereof, and biologically active fragments thereof, wherein the vIL-6 amino acid sequence is active in an assay for vIL-6 activity.

Recently, the crystal structure of vIL-6 has revealed that vIL-6 shares with other members of the IL-6 family the canonical up-up-down-down, ABCD four-helix bundle connected by peptide loops (Chow et al., *Science* 2001; 291: 2150-2155 (FIG. 9A). In that study, a soluble tetrameric complex (2:2) of vIL-6 and the three NH2-terminal domains (D1D2D3) of gp130 was crystallized in the absence of IL-6R. Based on this vIL-6-gp130 crystal complex, the unused site I face of vIL-6, where human IL-6 would interact with IL-6R, is not occupied by gp130 and is sterically accessible for engagement by another molecule (FIG. 9B).

According to the crystallographic analysis of the vIL-6/sgp130 (D1D2D3) complex (Chow et al., *Science* 2001; 291:2150-2155), sequence alignment of human and vIL-6 shows that contact residues seen in the structure of the vIL-6/gp130 complex are in the same positions as human IL-6-gp130 contact residues previously mapped by mutagenesis (Simpson et al., *Protein Sci* 1997; 6:929-955). In cell culture, the membrane-proximal extracellular part of gp130 (D4D5D6) is critical for vIL-6 mediated-signaling, even though vIL-6 can form a tetrameric complex with gp130 (D1D2D3) (Chow et al., *Science* 2001; 291:2150-2155). Further, although human and vIL-6 share an epitope in gp130 D2, vIL-6 does not appear to utilize an epitope in gp130 D3 that is critical to human IL-6 function.

Lentivirus: Lentiviruses are characterized by long incubation periods between infection of the host and the manifestation of clinical disease. Lentiviruses infect a wide variety of mammals, including humans, monkeys, sheep, goats, and horses. Includes for example retroviruses, such as immunodeficiency viruses, such as HIV-1, HIV-2, feline immunodifficency virus (FIV), and simian immunodifficiency virus (SIV).

The human immunodeficiency virus (HIV) is the etiological agent of the acquired immunodeficiency syndrome (AIDS) and related disorders. The expression of the virus in infected persons is regulated to enable the virus to evade the host's immune response. The HIV viruses (e.g. HIV-1 and HIV-2), as well as the simian immunodeficiency virus (SIV), share many structural and regulatory genes such as gag, pol, env, tat, rev and nef (see Guyader et al., *Nature* 328:662-669, 1987). HIV has been classified as a lentivirus because it causes slow infection, and has structural properties in common with such viruses (Haase, *Nature* 322:130-136, 1986).

Mammal: This term includes both human and non-human mammals. Similarly, the terms "subject," "patient," and "individual" includes human and veterinary subjects.

N-terminal region of a protein: Proteins are directional, and have an amino terminus (N-terminus), and a carboxy terminus (C-terminus). The amino terminal (N-terminal) portion of a protein is the portion of the protein near the N-terminus. In one embodiment, the N-terminal region is the half of the protein near to the N-terminus. The N-terminal region of a protein can include a receptor binding site of a protein, which is a region of a protein that interacts with the receptor. It should be noted that the C-terminal region of a protein can also include a receptor binding site.

In one embodiment, the N-terminal region of vIL-6 is about half of the vIL-6 polypeptide near the N-terminus, or from about amino acid 1 (numbering from the N-terminus) to about amino acid number 102 of wild-type vIL-6. In one specific, non-limiting example, an N-terminal region of vIL-6 includes about ten to about 20 amino acids of the N-terminal region of IL-6. In another specific, non-limiting example, the N-terminal region includes, but is not limited to, the vIL-6 fragment inclusive of $Asp^{81}$-$Cys^{93}$.

Neutralizing binding agents: A specific binding agent that is able to specifically bind to a target protein in such a way as to inhibit the subsequent biological functioning of that target protein is said to be neutralizing of that biological function. The inhibition can be at least a 40%, 50%, 60%, 75%, 85%, 90%, or 100% inhibition of the biological function. In general, any protein that can perform this type of specific blocking activity is considered a neutralizing protein; antibodies are therefore a specific class of neutralizing protein. The complex formed by binding of a neutralizing protein to a target protein is called a neutralizing complex.

In one embodiment, a neutralizing agent is an antibody. Antibodies that bind to viral components and thereby prevent the binding of the viral component to target host cells or a target protein and inhibit a biological function of the viral component are said to neutralize the viral component. Therefore, antibodies that bind to KSHV proteins and measurably reduce an activity of the virus are neutralizing antibodies. In one embodiment, a vIL-6 binding agent that binds the N-terminus of KSHV vIL-6 is neutralizing. In one embodiment, neutralizing antibodies bind a domain, such as about ten to about fifteen amino acids of the vIL-6 site I. In another embodiment, neutralizing antibodies bind about 13 amino acids of the vIL-6 site I, such as a region of the C-terminal part of the AB-loop and/or the beginning of helix B, although any antigenic determinant of the N-terminus can be utilized. In one specific, non-limiting example the 13 amino acids of the receptor binding site have a sequence as set forth as SEQ ID NO: 3, or a conservative variant thereof. The use of an antigenic region on a protein to provide epitopes appropriate for the natural or laboratory generation of neutralizing antibodies is known in the art (e.g. see WO 98/36087; U.S. Pat. Nos. 5,843,454; 5,695,927; 5,643,756; and 5,013,548).

Any assay for vIL-6 activity (see above) can be used to determine that a vIL-6 specific binding agent is neutralizing. The assay can be either an in vivo or an in vitro assay. Specific, non-limiting examples, of assays of use are an assay for the ability of vIL-6 to support the proliferation of mouse B9 cells. These assays are well known to one of skill in the art. Briefly, B9 cells (approximately 2,000 cells per well) are cultured in a series of microwells (e.g. in a 96 microwell plate). A series of dilutions (decreasing concentrations, generally about 2 fold serial dilutions) of the sample are added to the wells, and the cells are incubated with the sample (e.g. for 72 hours in a humidified 37° C., 5% $CO_2$ incubator). After incubation the cells are pulsed with $[^3H]$ thymidine (e.g. for 4 hours at 37° C.), and the amount of $[^3H]$thymidine incorporated is measured (e.g. by liquid scintillation counting). The measurement reflects the amount of biologically active IL-6 present in the sample. In general, a standard is used that contains a known level of IL-6 activity to assess normalization of inter-assay variation.

Other assays include an assay to determine the proliferation of the human myeloma cell line INA-6 (which is strictly dependent on exogenous IL-6 for growth and survival). Other assays of use are the stimulation the growth of KSHV-infected PEL cells (Jones et al., *Blood* 94:2871, 1999), the promotion of hematopoiesis (Aoki, et al., *Blood* 93:4034, 1999), and the activation of STAT1, STAT3 and JAK1 phosphorylation (Molden et al., *J Biol. Chem.* 272: 19625, 1997).

These assays are amenable to quantification and thus the percent stimulation or inhibition of targets can be measured. For example, in the in vitro B9 cell assay, B9 cell proliferation in medium without vIL-6 is typically 10-20 fold lower than in medium containing vIL-6. A vIL-6 neutralizing agent may abolish completely or in part B6 cell growth stimulation induced by vIL-6. The degree of inhibition of vIL-6 B9 cell growth stimulation by a neutralizing agent can be expressed as a percentage: 100% neutralization reflects a complete abrogation of B9 cell stimulation by vIL-6 whereas a 50% inhibition reflects abrogation of 50% B9 cell stimulation induced by vIL-6.

Pharmaceutical agent or drug: A chemical compound or composition capable of inducing a desired therapeutic or prophylactic effect when properly administered to a subject.

Pharmaceutically acceptable carriers: The pharmaceutically acceptable carriers useful in this invention are conventional. *Remington's Pharmaceutical Sciences*, by E. W. Martin, Mack Publishing Co., Easton, Pa., 15th Edition (1975), describes compositions and formulations suitable for pharmaceutical delivery of the specific binding agents for vIL-6 herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: any chain of amino acids, regardless of length or post-translational modification (e.g., glycosylation or phosphorylation).

Specific binding agent: An agent that binds substantially only to a defined target. In one embodiment, a specific binding agent is a neutralizing binding agent. In one embodiment, a specific binding agent is neutralizing. In one embodiment, a vIL-6 specific binding agent is a polypeptide, such as a gp130 polypeptide, or a fragment thereof. In another embodiment, a KSHV vIL-6 specific binding agent includes anti-vIL-6 antibodies and other agents that bind substantially only to vIL-6.

In one embodiment, a specific binding agent that binds vIL-6 is a neutralizing binding agent (e.g. a neutralizing antibody). Neutralizing antibodies may be monoclonal or polyclonal antibodies that are specific for v-IL6, and particularly its N-terminal domain, as well as immunologically effective portions ("fragments") thereof. In one embodiment, a specific binding agent of the invention are monoclonal antibodies (or immunologically effective portions thereof) and may also be humanized monoclonal antibodies (or immunologically effective portions thereof). Immunologically effective portions of monoclonal antibodies include Fab, Fab, F(ab)$_2$, Fabc and Fv portions (for a review, see Better and Horowitz, *Methods. Enzymol.* 1989, 178:476-496). Anti-vIL-6 peptide antibodies may also be produced using standard procedures described in a number of texts, including *Antibodies, A Laboratory Manual* by Harlow and Lane, Cold Spring Harbor Laboratory (1988), see below.

The determination that a particular agent binds substantially only to the vIL-6 peptide may readily be made by using or adapting routine procedures. One suitable in vitro assay makes use of the Western blotting procedure (described in many standard texts, including *Antibodies, A Laboratory Manual* by Harlow and Lane). Western blotting may be used to determine that a given binding agent, such as an anti-vIL-6 antibody, binds substantially only to KSHV vIL-6.

Variants of Amino Acid Sequences: One of ordinary skill in the art will appreciate that a DNA sequence can be altered in numerous ways without affecting the biological activity of the encoded protein, such as vIL-6. Conservative amino acid substitutions can preserve the functional and immunologic identity of the encoded polypeptide. Conservative substitutions replace one amino acid with another amino acid that is similar in size, hydrophobicity, etc. Examples of conservative substitutions are shown in Table 1 below.

TABLE 1

| Original Residue | Conservative Substitution |
| --- | --- |
| Ala | ser |
| Arg | lys |
| Asn | gln, his |
| Asp | glu |
| Cys | ser |
| Gln | asn |
| Glu | asp |
| Gly | pro |
| His | asn; gln |
| Ile | leu, val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

More substantial changes in protein function may be obtained by selecting amino acid substitutions that are less conservative than those listed in Table 4. Such changes include changing residues that differ more significantly in their effect on maintaining polypeptide backbone structure (e.g., sheet or helical conformation) near the substitution, charge or hydrophobicity of the molecule at the target site, or bulk of a specific side chain. The following substitutions are generally expected to produce the greatest changes in protein properties: (a) a hydrophilic residue (e.g., seryl or threonyl) is substituted for (or by) a hydrophobic residue (e.g., leucyl, isoleucyl, phenylalanyl, valyl or alanyl); (b) a cysteine or proline is substituted for (or by) any other residue; (c) a residue having an electropositive side chain (e.g., lysyl, arginyl, or histadyl) is substituted for (or by) an electronegative residue (e.g., glutamyl or aspartyl); or (d) a residue having a bulky side chain (e.g., phenylalanine) is substituted for (or by) one lacking a side chain (e.g., glycine).

Variant encoding sequences may be produced by standard DNA mutagenesis techniques, for example, M13 primer mutagenesis. Details of these techniques are provided in Sambrook et al. (In *Molecular Cloning: A Laboratory Manual*, CSHL, New York, 1989), Ch. 15. By the use of such techniques, variants may be created which differ in minor ways from the human sequences disclosed.

Alternatively, the coding region may be altered by taking advantage of the degeneracy of the genetic code to alter the coding sequence such that, while the nucleotide sequence is substantially altered, it nevertheless encodes a protein having an amino acid sequence substantially similar to the disclosed protein sequences. Based upon the degeneracy of the genetic code, variant DNA molecules may be derived from cDNA and gene sequences using standard DNA mutagenesis techniques as described above, or by synthesis of DNA sequences.

The immunologic identity of the protein may be assessed by determining whether it binds to a specific binding agent (e.g., a neutralizing antibody that binds vIL-6); a variant that is recognized by such an antibody is immunologically conserved. Any cDNA sequence variant will preferably introduce no more than 20, and preferably fewer than 10 amino acid substitutions into the encoded polypeptide. Variant amino acid sequences may, for example, be 80, 90 or even 95% identical to the native amino acid sequence.

DETAILED DESCRIPTION OF THE SPECIFIC EMBODIMENTS

Specific Binding Agents for vIL-6

Kaposi's sarcoma-associated herpesvirus interleukin-6 can be used to produce neutralizing agents that bind vIL-6. In one embodiment, these agents are antibodies which are immunoreactive or bind to epitopes or variants of vIL-6 and inhibit a biological function of vIL-6. Antibodies which consist essentially of pooled monoclonal antibodies with different epitopic specificities, polyclonal antibodies as well as distinct monoclonal antibody preparations are provided, as long as the antibodies interfere with a biological activity of vIL-6.

In one embodiment, the specific binding agent binds the N-terminus of KSHV vIL-6, and neutralizes an activity of vIL-6. In another embodiment, the specific binding agent binds a portion of vIL-6 in a region of the C-terminal part of the AB-loop and/or the beginning of helix-B, and thus neutralizes an activity of vIL-6. In one specific, non-limiting example, the specific binding agent binds about ten to about fifteen amino acids, although the specific binding agent can bind number of amino acids in the region. In one embodiment, the monoclonal antibody induces a conformational change that affects the binding of vIL-6 and gp130.

In one embodiment, the specific binding agent binds a region of vIL-6 in the N-terminal portion of vIL-6. In one specific, non-limiting example, the specific binding agent binds about ten to about twenty amino acids of the N-terminal portion of vIL-6. For example, the specific binding agent binds about thirteen amino acids of the N-terminal portion of vIL-6, such as DHCGLIGFNETSC (SEQ ID NO: 3), or a conservative variant thereof, and wherein binding of the specific binding agent neutralizes an activity of vIL-6. In a specific non-limiting examples, the monoclonal antibody specifically binds a domain within the vIL-6 site I, such as a region of the C-terminal part of the AB-loop and/or the beginning of helix-B.

The specific binding agent can be a polypeptide or a fragment thereof, a chemical or pharmaceutical compound, or an antibody.

The preparation of polyclonal antibodies is well-known to those skilled in the art. See, for example, Green et al., "Production of Polyclonal Antisera," in: *Immunochemical Protocols* pages 1-5, Manson, ed., Humana Press 1992; Coligan et al., "Production of Polyclonal Antisera in Rabbits, Rats, Mice and Hamsters," in: *Current Protocols in Immunology*, section 2.4.1, 1992, which are hereby incorporated by reference.

The preparation of monoclonal antibodies likewise is conventional. See, for example, Kohler & Milstein, *Nature* 256:495, 1975; Coligan et al., sections 2.5.1-2.6.7; and Harlow et al., in: *Antibodies: a Laboratory Manual*, page 726, Cold Spring Harbor Pub., 1988, which are hereby incorporated by reference. Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan et al., sections 2.7.1-2.7.12 and sections 2.9.1-2.9.3; Barnes et al., "Purification of Immunoglobulin G (IgG)," in: *Methods in Molecular Biology*, Vol. 10, pages 79-104, Humana Press, 1992.

Methods of in vitro and in vivo multiplication of monoclonal antibodies are well known to those skilled in the art. Multiplication in vitro may be carried out in suitable culture media such as Dulbecco's Modified Eagle Medium or RPMI 1640 medium, optionally supplemented by a mammalian serum such as fetal calf serum or trace elements and growth-sustaining supplements such as normal mouse peritoneal exudate cells, spleen cells, thymocytes or bone marrow macrophages. Production in vitro provides relatively pure antibody preparations and allows scale-up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells, e.g., syngeneic mice, to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the animal.

Therapeutic applications for antibodies disclosed herein are also part of the present invention. Thus, antibodies of the present invention may also be derived from subhuman primate antibody. General techniques for raising therapeutically useful antibodies in baboons can be found, for example, in Goldenberg et al., International Patent Publication WO 91/11465, 1991, and Losman et al., *Int. J. Cancer* 46:310, 1990).

Alternatively, a therapeutically useful anti-vIL-6 neutralizing antibody may be derived from a "humanized" monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Nat'l Acad. Sci. USA* 86:3833, 1989). Techniques for producing humanized monoclonal antibodies are described, for example, by Jones et al., *Nature* 321:522, 1986; Riechmann et al., *Nature* 332:323, 1988; Verhoeyen et al., *Science* 239:1534, 1988; Carter et al., *Proc. Nat'l Acad. Sci. USA* 89:4285, 1992; Sandhu, *Crit. Rev. Biotech.* 12:437, 1992; and Singer et al., *J. Immunol.* 150:2844, 1993.

Antibodies of the invention also may be derived from human antibody fragments isolated from a combinatorial immunoglobulin library. See, for example, Barbas et al., in: *Methods: a Companion to Methods in Enzymology*, Vol. 2, page 119, 1991; Winter et al., *Ann. Rev. Immunol.* 12:433, 1994, which are hereby incorporated by reference. Cloning and expression vectors that are useful for producing a human immunoglobulin phage library can be obtained, for example, from STRATAGENE Cloning Systems (La Jolla, Calif.).

In addition, antibodies may be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7:13, 1994; Lonberg et al., *Nature* 368:856, 1994; and Taylor et al., *Int. Immunol.* 6:579, 1994.

Neutralizing antibodies used include intact molecules as well as fragments thereof, such as Fab, $F(ab')_2$, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) $(Fab')_2$, the fragment of the antibody that can be obtained by treating whole antibody with the enzyme pepsin without subsequent reduction; $F(ab')_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art (See for example, Harlow and Lane, *Antibodies: A Laboratory Manual*, Cold Spring Harbor Laboratory, New York, 1988, incorporated herein by reference). Antibody fragments can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein; Nisonhoff et al., *Arch. Biochem. Biophys.* 89:230, 1960; Porter, *Biochem. J.* 73:119, 1959; Edelman et al., *Methods in Enzymology*, Vol. 1, page 422, Academic Press, 1967; and Coligan et al. at sections 2.8.1-2.8.10 and 2.10.1-2.10.4.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of $V_H$ and $V_L$ chains. This association may be noncovalent, as described in Inbar et al., *Proc. Nat'l Acad. Sci. USA* 69:2659, 1972. Alternatively, the variable chains can be linked by an intermolecular disulfide bond or cross-linked by chemicals such as glutaraldehyde. See, e.g., Sandhu, supra. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow et al., *Methods: a Companion to Methods in Enzymology*, Vol. 2, page 97, 1991; Bird et al., *Science* 242:423-426, 1988; Ladner et al., U.S. Pat. No. 4,946,778; Pack et al., *Bio/Technology* 11: 1271-77, 1993; and Sandhu, supra.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (see, for example, Larrick et al., *Methods: a Companion to Methods in Enzymology*, Vol. 2, page 106, 199).

Antibodies which bind to vIL-6, a variant thereof, or a biologically active fragment thereof, can be prepared using an intact polypeptide or fragments containing small peptides of interest as the immunizing antigen. In one embodiment, the N-terminus of vIL-6 is utilized to prepare antibodies that bind to vIL-6. In another embodiment, a polypeptide that encompasses a region of the C-terminal part of the AB-loop and the beginning of helix-B is utilized. In one specific, non-limiting example, about ten to about twenty amino acids are utilized, although any antigenic determinant of the N-terminus can be utilized. In one specific, non-limiting example the thirteen amino acids are utilized that have a sequence as set forth as SEQ ID NO: 3, or a conservative variant thereof.

The polypeptide or a peptide used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, for example, by binding to and elution from a matrix to which the polypeptide or a peptide to which the antibodies were raised is bound. Various techniques are common in the immunology arts for purification and/or concentration of polyclonal antibodies, as well as monoclonal antibodies (See for example, Coligan et al., Unit 9, *Current Protocols in Immunology*, Wiley Interscience, 1991).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

Cell-Free Assay for Testing the Efficacy of a Neutralizing Agent

In order to test the efficacy of an agent for treating or detecting a KSHV associated disorder a cell free system has been developed. This cell free system includes isolated vIL-6 and a receptor component that binds vIL-6 (e.g. gp130). The binding of vIL-6 and the vIL-6 receptor component in the presence of the agent is compared to binding of vIL-6 to the vIL-6 receptor component in the absence of the agent. A decrease in the binding of vIL-6 to the receptor component in the presence of the agent indicates that the agent is neutralizing, and thus is effective for treating a KSHV-associated disorder.

In one embodiment, the method includes incubating agents and a sample containing vIL-6 and a receptor component that binds vIL-6 under conditions sufficient to allow the components to interact, and measuring the effect of the compound on the interaction of the receptor component and vIL-6. Agents which specifically bind vIL-6 and affect the interaction of the receptor component and vIL-6 include peptides, polypeptides, chemical compounds and biological agents. In one specific, non-limiting example, the receptor component is gp130. In another specific, non-limiting example, the agent is a polypeptide fragment of gp130. Antiviral, immunosuppressive, and chemotherapeutic compounds can be tested using the method of the invention.

Incubating includes any conditions that allow contact between the test agent, vIL-6 and the receptor component (e.g. gp130). "Contacting" includes in solution and solid phase. The test compound may also be a combinatorial library for screening a plurality of compounds. Compounds identified in the method of the invention can be further evaluated, detected, cloned, sequenced, and the like, either in solution of after binding to a solid support, by any method usually applied to the detection of a specific DNA sequence, such as PCR, oligomer restriction (Saiki et al., *Bio/Technology* 3:1008-1012, 1985), allele-specific oligonucleotide (ASO) probe analysis (Conner et al., *Proc. Natl. Acad. Sci. USA* 80:278, 1983), oligonucleotide ligation assays (OLAs) (Landegren et al., *Science* 241:1077, 1988), and the like. Molecular techniques for DNA analysis have been reviewed (Landegren et al., *Science* 242:229-237, 1988).

The binding affinities of agents which affect the interaction of the receptor component with vIL-6 can also be determined. In these assays, a labeled ligand is employed. A number of labels have been indicated previously (e.g., radiolabels, fluorescence labels, among others) to be of use. The candidate compound is added in an appropriate buffered medium. After an incubation to ensure that binding has occurred, the surface may be washed free of any nonspecifically bound components of the assay medium, particularly any nonspecifically bound labeled ligand, and any label bound to the surface determined. The label may be quantitatively measured. By using standards, the relative binding affinity of a candidate compound can be determined.

Detection or Treatment of a KSHV Associated Disorder

The specific binding agents (e.g. neutralizing antibodies) that bind vIL-6 can be used to detect or treat a KSHV-associated disorder or a KSHV-related disorder. The term "KSHV-associated disorder" denotes any disorder associated with KHSV infection, including, but not limited to, Kaposi's sarcoma, primary effusion lymphoma (PEL), and Castleman's disease.

The specific binding agents that neutralize a biological activity of vIL-6 can be used to determine the prognosis of a KSHV-associated disorder. They can also be useful in guiding choices between different treatment regimens in patients with KSHV-associated or -related disorders. The "prognosis" is a forecast as to the probable outcome of an attack of a disease; the prospect as to recovery from a disorder as indicated by the nature and symptoms of the case. In addition, the specific binding agents for vIL-6 may be used to identify or treat individuals who are "at risk" of developing a KSHV-associated disorder. These individuals may be identified by a method of the invention for detecting the presence or absence of KSHV vIL-6 or by any other diagnostic means, and/or may be treated with the specific binding agent that neutralizes a biological activity of vIL-6, prior to the actual onset of the clinical appearance (any sign or symptom) of disorder.

An antibody or other specific binding agent that neutralizes a biological activity of vIL-6 can be used to detect vIL-6 polypeptide in subject samples such as biological fluids, cells, tissues, or nucleic acid. Any specimen containing a detectable amount of antigen (vIL-6) can be used. Examples of biological fluids of use with the invention are blood, serum, plasma, urine, mucous, and saliva. Tissue, cell samples, or extracts thereof can also be used with the subject invention. The samples can be obtained by many methods such as cellular aspiration, or by surgical removal of a biopsy sample.

The invention provides a method for detecting vIL-6, which comprises contacting a specific binding agent that neutralizes a biological activity of vIL-6 with a sample suspected of containing vIL-6, and detecting binding of the specific binding agent to vIL-6 in the sample. The specific binding agent that neutralizes a biological activity of vIL-6 is preferably labeled with a compound which allows detection of binding to vIL-6. The level of vIL-6 in the subject sample can be compared with the level in a sample not affected by the disease process. The sample not affected by the disease process can be taken from a control subject not affected by the disease process, or can be from a cell line, or can be a blank control (medium).

The specific binding agents that neutralize a biological activity of vIL-6 can be used in any subject in which it is desirable to administer in vitro or in vivo immunodiagnosis or immunotherapy. For example, neutralizing antibodies of the invention are suited for use, for example, in immunoassays in which they can be utilized in liquid phase or bound to a solid phase carrier. In addition, the antibodies in these immunoassays can be detectably labeled in various ways. Examples of types of immunoassays which can utilize antibodies of the invention are competitive and non-competitive immunoassays in either a direct or indirect format. Examples of such immunoassays are the radioimmunoassay (RIA) and the sandwich (immunometric) assay (e.g. ELISA). Those of skill in the art will know, or can readily discern, an appropriate immunoassay format without undue experimentation.

The neutralizing antibodies of the invention can be bound to many different carriers, both soluble and insoluble, and used to detect the presence of vIL-6. Examples of well-known carriers include glass, polystyrene, polypropylene, polyethylene, dextran, nylon, amylases, natural and modified celluloses, polyacrylamides, agaroses and magnetite. Those skilled in the art will know of other suitable carriers for binding antibodies, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, phosphorescent compounds, and bioluminescent compounds. Those of ordinary skill in the art will know of other suitable labels for binding to the antibody, or will be able to ascertain such, using routine experimentation.

Another technique which may also result in greater sensitivity consists of coupling the antibodies to low molecular weight haptens. These haptens can then be specifically detected by means of a second reaction. For example, it is common to use such haptens as biotin, which reacts with avidin, or dinitrophenyl, puridoxal, and fluorescein, which can react with specific antihapten antibodies.

In using the antibodies that specifically bind vIL-6 and neutralize a biological activity of vIL-6 for the in vitro or in vivo detection of antigen, the detectably labeled antibody is given a dose which is diagnostically effective. The antibodies that specifically bind vIL-6 and neutralize an activity of vIL-6 can be used in vitro and in vivo to monitor the course of amelioration of a KSHV-associated disorder in a subject. Thus, for example, by measuring the changes in the concentration of vIL-6 in various body fluids, it would be possible to determine whether a particular therapeutic regimen aimed at ameliorating the KSHV-associated disease is effective. The term "ameliorate" denotes a lessening of the detrimental effect of the KSHV-associated disease in the subject receiving therapy.

Kits

The specific binding agents are ideally suited for the preparation of a kit. Such a kit may comprise a carrier such as a box or a bag made of any material (e.g., plastic or paper) containing one or more containers such as vials, tubes, and the like, each of the container means comprising one of the separate elements to be used in the method. One of the containers can include a specific binding agent that neutralizes an activity of vIL-6 which is or can be detectably labeled. In one specific, non-limiting example, the binding agent is an antibody, or specific fragment thereof, that neutralizes an activity of vIL-6. For example, an antibody that neutralizes an activity of vIL-6 can be included in a kit and used for examining the presence of vIL-6 in a sample, as well as a control sample for comparison. Thus, the binding of the neutralizing antibody with a test sample from a subject of interest can then be compared with the binding of the neutralizing antibody with the control included in the kit. The relative degree of binding to the sample as compared to the control indicates infection with KSHV, or the likelihood for an subject developing a KSHV-associated disorder.

The kit can also contain a container including a second antibody which binds to the antibody that specifically binds and neutralizes an activity of vIL-6. The second antibody can be directly labeled. Alternatively, the kit may also be a container including a reporter molecule, such as avidin or steptavin, bound to a molecule such as an enzymatic, fluorescent, or radionucleotide label to identify the directly labeled second antibody.

The kit can also contain directions for use. This includes written instructions or instructions in an electronic format, such as on a diskette or CD-rom disk.

EXAMPLES

Without further elaboration, it is believed that one skilled in the art can, using this description, utilize the present invention to its fullest extent. The following examples are illustrative only, and not limiting of the remainder of the disclosure in any way whatsoever.

Example 1

Materials and Methods

Preparation of recombinant vIL-6 and its deletion mutants: Recombinant vIL-6 was prepared as a fusion protein that has a factor Xa cleavage site between the amino terminal tag of maltose binding protein (MBP) and amino acids 22-204 of vIL-6 (MBPvIL-6) (Aoki et al., *Blood* 93:4034, 1999). Deletion mutants of vIL-6 were prepared as follows: vIL-6 M1 and M2 were constructed by inserting a stop codon at positions 37 and 81, respectively. After denaturing, pMALvIL-6 was annealed with the following mutagenesis oligonucleotides:

```
M1: ATTTAGATCTTCAATTGGATGCTA (SEQ ID NO:5);

M2: ACTTAGATCTGCGGGTTAATAGGA (SEQ ID NO:6) ;
``` that encode a restriction enzyme site for Bgl II as well as stop codons, and mutant strands were synthesized using GeneEditor in vitro site-directed mutagenesis system (Promega, Madison, Wis.). After transformation, positive colonies were screened by GeneEditor and Bgl II digestion. vIL-6 M3 and M5 were constructed by restriction enzyme digestion of pMALvIL-6 with Aat II and EcoRI, respectively, followed by ligation. To construct expression vectors for vIL-6 M4, M6 and M7, fragments including the C-terminus of vIL-6 were amplified using the following oligonucleotide primers: M4-Bam HI: ACTGGATCCCT-TAAAAAGCTCGCCGAT (SEQ ID NO:7); M6-Bam HI: TTTGGATCCTTAACGACGGAGTTTGGA (SEQ ID NO:8); M7-Bam HI: ACGGGATCCAGTCCAC-CCAAATTTGAC (SEQ ID NO:9) and vIL-6-3'-Hind CCCAAGCTTATTACTTATCGTGGACGT (SEQ ID NO:10). After digestion with Bam HI and Hind HI, the PCR products were ligated into pMAL-c2 (New England BioLabs, Beverly, Mass.). All recombinant protein-expressing clones were analyzed by DNA sequence analysis, and expressed in *Escherichia coli* strain DH5α (Life Technologies, Gaithersburg, Md.). Large-scale production and affinity purification of fusion proteins were performed according to the manufacturer's instructions.

Generation of mAbs against vIL-6: To generate mAbs against vIL-6, mice were immunized with MBPvIL-6. After boosting, splenocytes were obtained for hybridoma production by standard procedures. Hybridomas were screened by enzyme-linked immunosorbent assay (ELISA) and Western blotting against recombinant vIL-6. Following bulk culture, mAbs were purified from culture supernatants using protein G columns (Pierce, Rockford, Ill.). The isotype of each mAb was determined using Mouse Typer sub-isotyping kit (Bio-Rad, Hercules, Calif.), according to the manufacture's instructions.

Western blotting: Immunoblotting of vIL-6 was performed as described previously (Jones, *Blood* 94:2871, 1999). Briefly, 100 ng of MBPvIL-6 cleaved with factor Xa (New England BioLabs), recombinant hIL-6 (a kind gift from Sandoz Pharmaceuticals) and recombinant mIL-6 (PeproTech, Rocky Hill, N.J.) were loaded onto each well of 10-20% tricine-SDS gel (NOVEX, San Diego, Calif.) after boiling for 10 minutes. The separated proteins were transferred onto polyvinylidene fluoride membranes (Immobilon-P; Millipore, Bedford, Mass.). Immunostaining was performed using rabbit polyclonal Abs against MBPvIL-6 (Aoki et al., *Blood*. 93:4034, 1999), mIL-6 (PeproTech) or mouse anti-vIL-6 mAbs followed by incubation with HRP-conjugated anti-mouse or rabbit IgG Abs (Amersham, Piscataway, N.J.). Immunocomplexes were visualized using the chemiluminescence detection system (Amersham).

Mapping the epitopes recognized by the monoclonal antibodies: Full length and deletion mutants of vIL-6 fusion proteins were immobilized onto 96-well plates (Immulon 4HBX; Dynex Technologies, Chantilly, Va.) in phosphate buffered saline (PBS) by overnight incubation at 4° C. After blocking nonspecific binding with SuperBlock (Pierce), a standard ELISA protocol was followed (Kellam et al., *J. Virol.* 73:5149, 1999; Jones et al., *J Exp Med.* 182:1213, 1995) using appropriate dilutions of anti-vIL-6 Ab and a1:500 dilution of goat anti-mouse polyvalent Ig conjugated to alkaline phosphatase (Sigma, St Louis, Mo.). Reactions were visualized by using p-nitrophenyl phosphate (Sigma), and plates were read at 405 nm with λ correction at 550 nm using a microplate reader.

vIL-6 bioassays: The B9 cell proliferation assay was performed essentially as described (Jones et al., *J Exp Med.* 182:1213, 1995). B9 cells ($2\times10^3$ cells/well) were incubated in 96-well plates (200 μl/well) with MBPvIL-6 (100 ng/ml)

and anti-vIL-6 mAbs (0 to 10 μg/ml) for 72 h at 37° C., including a 6-h terminal pulse with 1 μCi/well of [$^3$H]-thymidine (Amersham, Arlington Heights, Ill.). [$^3$H]-thymidine incorporation was determined after cell harvesting onto glass fiber filters. The SKW6.4 IgM secretion assay was performed essentially as described (Peppard et al., *Biol. Chem.* 271:7281, 1996). SKW6.4 cells (1×10$^4$ cells/well) were incubated in 96-well plates(200 μl/well) with MBPvIL-6 (0 to 4 μg/ml) or hIL-6 (0 to 20 ng/ml) with or without anti-vIL-6 mAbs (0 to 10 μg/ml) for 96 h at 37° C. IgM levels in the culture supernatants were measured using a human IgM ELISA quantitation kit (Bethyl Laboratories Inc, Montgomery, Tex.), according to the manufacturer's instructions. This ELISA does not detect murine IgG.

Figure 6:
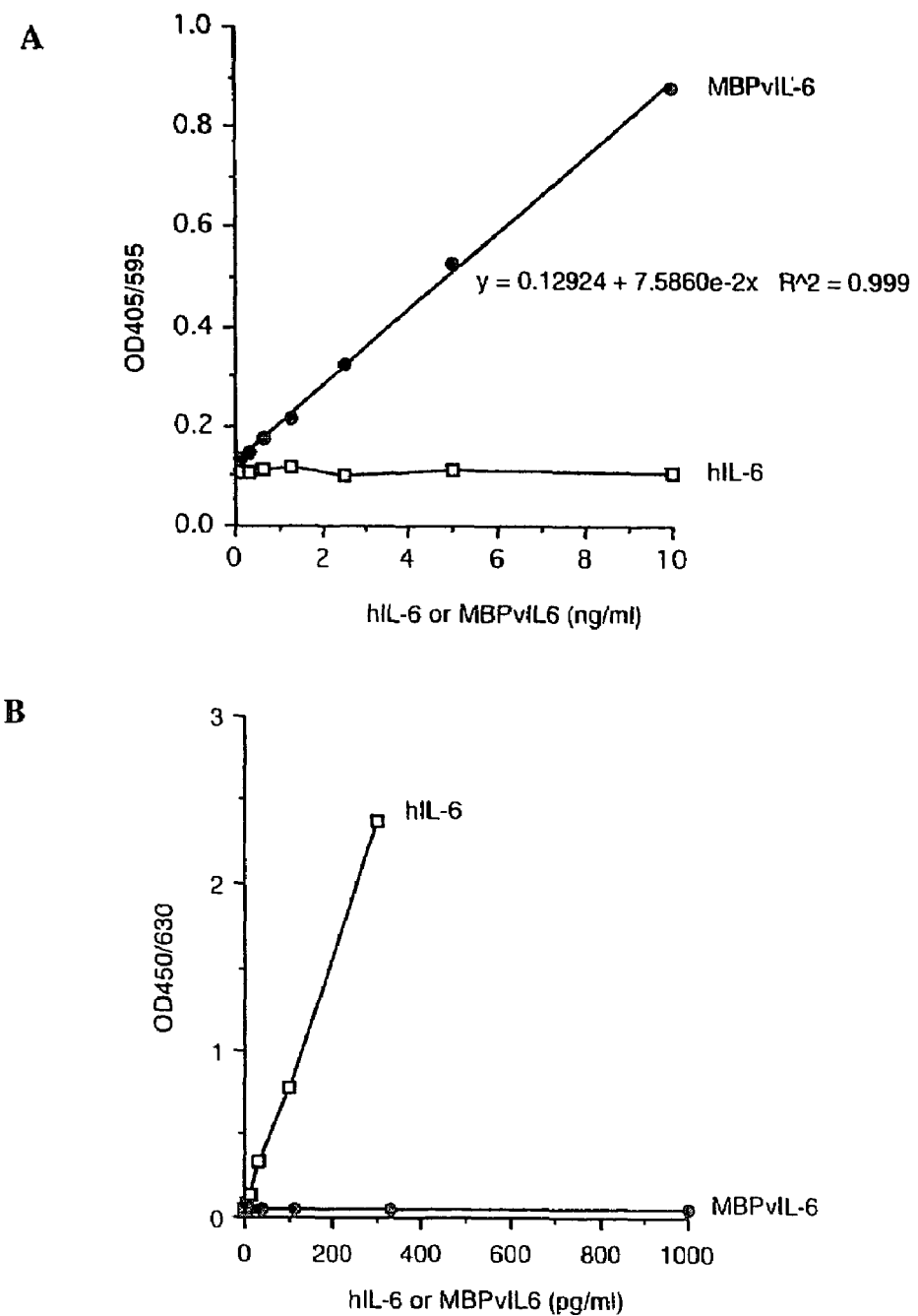
FIG. 6 is a set of two graphs demonstrating antibody specificity for vIL-6 and establishment of a vIL-6 ELISA.

ELISA-based binding assay: The binding of vIL-6 to IL-6Rα was analyzed by ELISA (FIG. 6) as described previously with some modifications (*J Biol Chem.* 273:21374, 1998). Purified recombinant human sIL-6Rα (R&D Systems, Minneapolis, Minn.) and human sgp130 (R&D Systems) were immobilized on ELISA plate wells (Immunol 4HBX) at 5 μg/ml in PBS. After blocking the plate with SuperBlock, MBPvIL-6 or hIL-6 were applied at 50 ng/ml in 1% BSA/PBS, and incubated for 5 h at room temperature. Bound protein was detected with polyclonal rabbit Abs directed against vIL-6 or hIL-6 (Pepro Tech) at 1 μg/ml, followed by an HRP-conjugated anti-rabbit IgG (Bio-Rad) at 1:3000 in PBS/0.05% Tween 20. Reactions were visualized by using tetramethoxybenzene peroxidase substrate (Kirkegaard & Perry Laboratories, Gaithersburg, Md.), followed by 2N H2SO4. The interference of vIL-6 binding to sgp130 by mAbs was analyzed in a similar manner. Biotinylated MBPvIL-6 (Jones et al., *Blood* 94:4034, 1999) was incubated at 50 ng/ml in 1% BSA/PBS with anti-vIL-6 mAbs or isotype control murine IgG1 (20 μg/ml) overnight at 4° C. The mixture was applied to the plates coated with sgp130 (2 μg/ml) after SuperBlock treatment. The protein complex was detected by streptavidin-HRP (1:1000; Kirkegaard & Perry Laboratories), and the peroxidase activity was visualized by tetramethoxybenzene peroxidase substrate, followed by 2N H$_2$SO$_4$. Plates were read at 450 nm with λ correction at 630 nm using a microplate reader.

Surface plasmon resonance: Biospecific interaction analysis was monitored by surface plasmon resonance using BIAcore 2000 system (Biacore AB, Uppsala, Sweden). sgp130-Fc (R&D systems), a fusion protein of sgp130 and human IgG Fc, was immobilized onto the CM5 (carboxymethylated dextran matrix) sensor chip using the amine coupling kit (BIAcore AB), and unreactive groups on the chip were blocked by ethanolamine according to the manufacturer's instructions. A continuous flow (10 μL/mL) of human IL-6 or MBPvIL-6 onto immobilized sgp130-Fc was monitored by passing the analytes across the sensor chip. In parallel experiments, sIL-6R was incubated with human IL-6 and MBPvIL-6 prior to assay. In comparative experiments, a continuous flow (20 μL/mL) of sIL-6R onto immobilized human IL-6 or MBPvIL-6 was monitored in the same manner. The sensor surface was regenerated between assays by 30 seconds treatment of 10 mM Glycine pH 2.2. BIAevaluation 3.0 software (BIAcore AB) was used for all the interaction analyses. The kinetics parameter was calculated according to a 1:1 Langmuir binding model (A+B N⇌AB) by direct fitting of ligand binding sensorgrams at multiple concentrations. The dissociation equilibrium constant is defined as dissociation constant (Kd)=dissociation rate constant ($k_d$)/association rate constant ($k_a$). The Kd was also determined by Scatchard analysis of equilibrium-state data obtained by a continuous flow (1 μL/mL) of MBPvIL-6 (50-800 μg/mL) onto immobilized sgp130-Fc, according to previously published methods (Ward et al., *Biochemistry* 1995; 34:2901-2907).

Example 2

Binding of vIL-6 to sgp130 in the Absence of sIL-6Rα

It is known that gp130 is involved in the signal transduction events which follow cell stimulation with vIL-6 (Nicholas et al., *Nat Med.* 3:287, 1997; Molden et al., *J Biol Chem.* 272:19625, 1997; Hideshima et al., *Clin Cancer Res.* 6:1180, 2000; Burger et al., *Blood* 91:1858, 1998; Wan et al., *J Virol.* 73:8268, 1999; Gage et al., *AIDS* 13:1851, 1999; Mullberg et al., *Immunol.* 164:4672, 2000). In contrast, the usage of IL-6Rα by vIL-6 is still controversial. Soluble forms of IL-6Rα and gp130, lacking the transmembrane and cytoplasmic regions, have been detected in human sera and body fluids (Peters et al., *Blood* 92:3495, 1998; Murakami-Mori et al., *Int Immunol.* 8:595, 1996) and have been produced as recombinant proteins. sIL-6Rα, when complexed with IL-6, acts agonistically on cells that express gp130, whereas sgp130 acts as an antagonist for IL-6 signaling (Taga et al., *An. Rev. Immunol.* 15:797, 1997; Peters et al., *Blood* 92:3495, 1998). It was investigated whether vIL-6 could bind to purified sIL-6Rα and sgp130 in a cell-free system. Purified human sIL-6Rα and/or sgp130 were immobilized onto a 96-well dish, and vIL-6 binding was assayed by indirect ELISA. As expected, hIL-6 bound to sIL-6Rα but not to sgp130 alone. When sIL-6Rα and sgp130 were first incubated and then immobilized onto wells, the binding of hIL-6 was slightly reduced (FIG. 1). By contrast, MBPvIL-6 bound to wells coated with sgp130 but not to wells coated with sIL-6Rα alone. The binding of vIL-6 to sgp130 was minimally affected by pre-incubation of sgp130 with sIL-6Rα. In parallel experiments, sIL-6Rα and sgp130 immobilized on a plate failed to bind to MBP.

Figure 10:
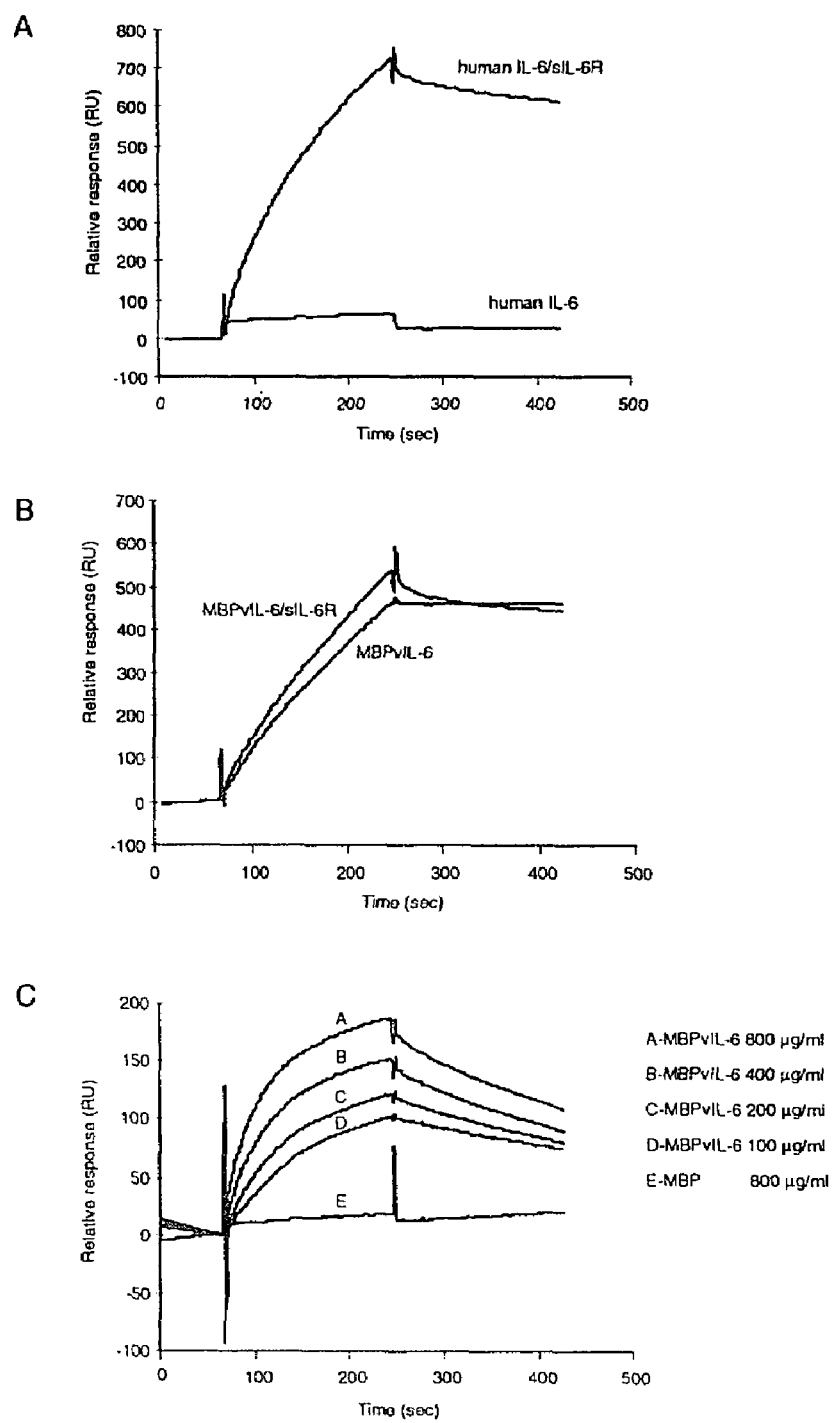
FIG. 10 is a set of graphs showing binding of human IL-6 or vIL-6 to immobilized sgp130 using the biosensor system BIAcore 2000. sgp130 was immobilized at a concentration of 18.2 ng/mm2 on the CM5 biosensor chip. (A) Human IL-6 (50 µg/mL) alone or human IL-6 (50 µg/mL) plus sIL-6R (20 µg/mL), (B) MBPvIL-6 (50 µg/mL) alone or MBPvIL-6 (50 µg/mL) plus sIL-6R (20 µg/mL) were passed over the sensor surface at a flow rate of 10 µl/min in PBS. Reagents were incubated for 1 hour prior to assay. (C) Overlay of sensorgrams showing kinetic analysis of vIL-6 with sgp130. sgp130 was immobilized at a concentration of 1.5 ng/mm2. MBPvIL-6 (100, 200, 400 and 800 µg/mL) was passed over the sensor surface. Control MBP (800 µg/mL) did not show detectable affinity for sgp130. Representative data of four independent experiments are shown.

Lack of IL-6R contribution to vIL-6/gp130 binding was further confirmed by surface plasmon resonance. The CM5 sensor chip immobilized with sgp130 was used for equilibrium binding analysis on the BIAcore system. Human IL-6 showed strong binding to sgp130 only when preincubated with sIL-6R (FIG. 10A). In contrast, vIL-6 bound to sgp130 without sIL-6R, and vIL-6 preincubation with sIL-6R minimally increased binding affinity for sgp130 (FIG. 10B). In accordance with these observations, sIL-6R bound to the CM5 sensor chip immobilized with human IL-6 but not MBPvIL-6 even though MBPvIL-6 was used at up to 2.2-times higher amount than that of human IL-6. A range of MBPvIL-6 concentrations was injected over the immobilized surface of sgp130, and, as a control, MBP (FIG. 10C). Control MBP showed minimal signal increase over base line. Binding of MBPvIL-6 to sgp130 demonstrated concentration dependence and saturability. Using a 1:1 Langmuir binding model, sensograms yielded a $k_a$ of 980 1/Ms, $k_d$ of 2.2×10$^{-3}$ 1/s and Kd of 2.2 μM. Additional BIAcore data of MBPvIL-6 binding to immobilized sgp130 at equilibrium was analyzed by Scatchard analysis. Using this method, the Kd for the vIL-6-gp130 interaction was calculated at 2.5 μM, which is comparable to the Kd obtained by the 1:1 Langmuir binding model. Previously, the affinity of human IL-6/sIL-6R complex for gp130 yielded a Kd of 1.7 nM.[36] Thus, the binding affinity of vIL-6 for sgp130 is 1000-fold lower than that of human IL-6/sIL-6R complex to gp130. Together, these experiments demonstrate that vIL-6 can bind to gp130 but not IL-6R.

Example 3

Generation of mAbs Against KSHV vIL-6: Epitope Mapping

To investigate further vIL-6 interactions with its receptor, vIL-6-specific mAbs were generated. Mice were immunized with the fusion protein of vIL-6 and MBP, MBPvIL-6 that was purified from *Escherichia coli* (Aoki et al., *Blood* 93:4034, 1999). Hybridomas were screened by ELISA against vIL-6 protein that was obtained from supernatants of NIH3T3 cells stably transfected with vIL-6 (Aoki et al., supra). Following a second screening, six anti-vIL-6 mAbs with IgG1 isotype were selected. It was first determined if these Abs recognize vIL-6 by Western blotting. All six mAb recognized vIL-6 protein that was obtained by cleaving MBPvIL-6 with factor Xa (Jones et al., *Blood* 94:2871, 1999). These Abs also detected vIL-6 in cell lysates of the KSHV-positive PEL cell line BCP-1 (Moore et al., *Science* 274:1739, 1996) but not in the control KSHV-negative Daudi cells by Western blotting. Although vIL-6 exhibits 25% amino acid identity to cellular IL-6, none of these mAbs recognized either hIL-6 or mIL-6. A rabbit polyclonal antiserum raised against vIL-6 recognized vIL-6 but not hIL-6 or mIL-6, whereas a rabbit polyclonal antiserum raised against murine IL-6 (mIL-6) recognized mIL-6 and hIL-6, but not vIL-6. These results suggest that the highly immunogenic epitopes on vIL-6 are distinct from those of cellular IL-6.

Example 4

An Assay for Neutralizing Activity of mAbs in IL-6-responsive Cell Lines

Figure 2:
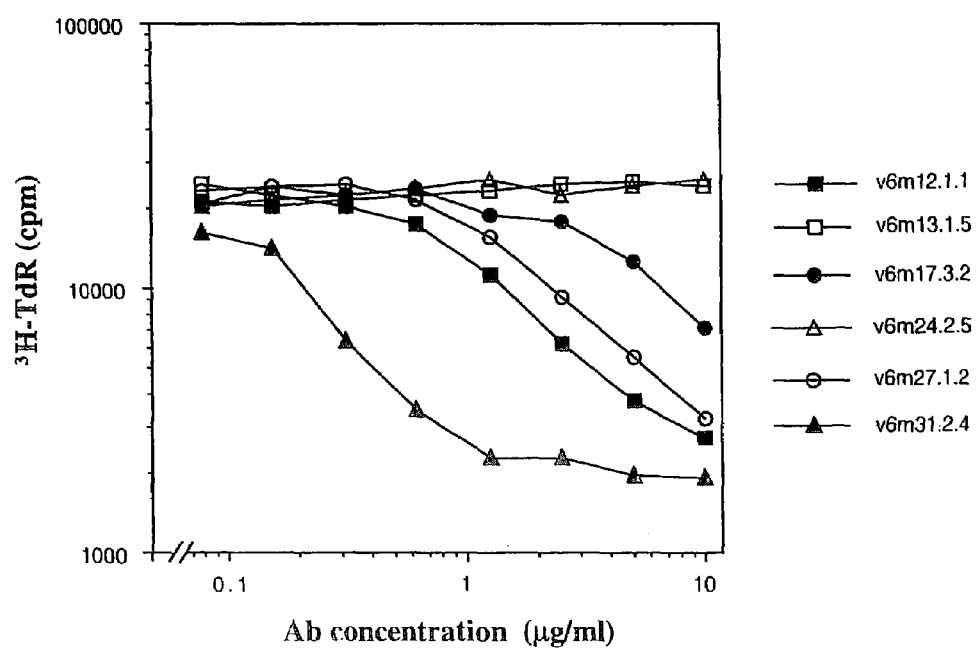
FIG. 2 is a graph of the neutralizing activity of mAbs against vIL-6 in the B9 cell bioassay. Exponentially growing B9 cells ($2\times10^3$ cells/well) were cultured in medium supplemented with MBPvIL-6 (100 ng/ml) with or without monoclonal anti-vIL-6 Ab (0.8 to 10 µg/ml). [$^3$H]-thymidine was added during the final 6 hours of culture. The results represent the mean radioactivity of triplicate cultures; SDs were within 5% of the mean. Representative data of two independent experiments are shown.
Figure 3:
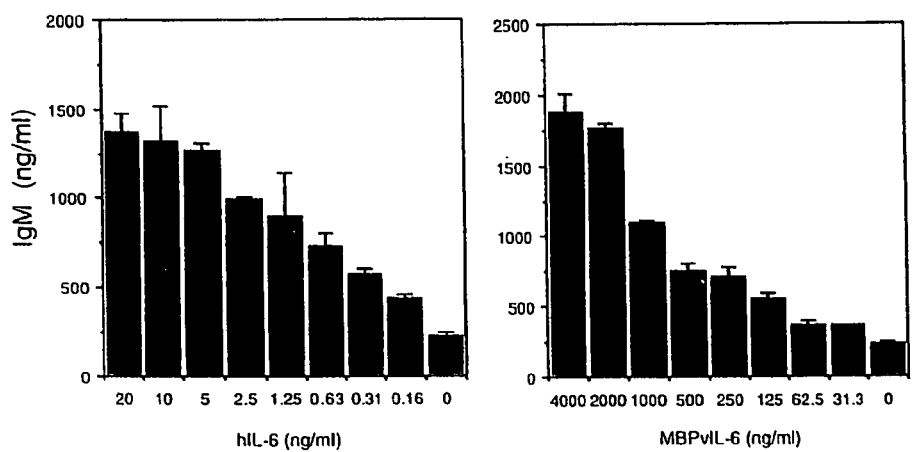
FIG. 3 is a series of bar graphs demonstrating the effect of mAbs against vIL-6 on IgM secretion by SKW6.4 cells.
Figure 3:
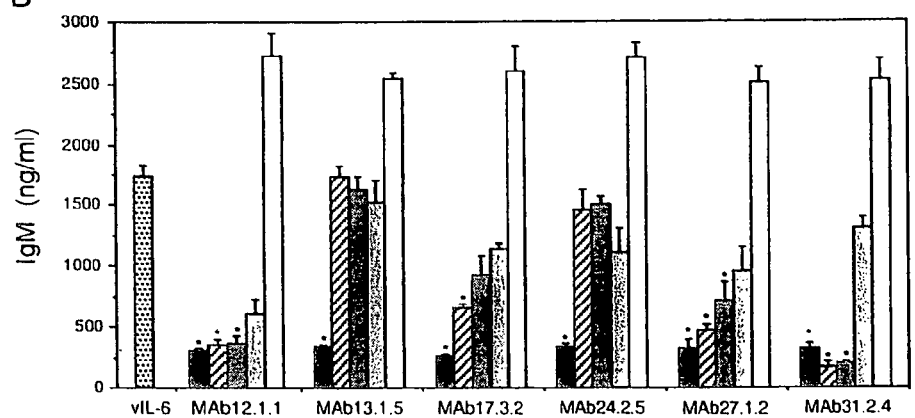

In order to assess if these mAbs neutralize vIL-6 bioactivities, a B9 proliferation assay was utilized (FIG. 2). vIL-6 has previously been shown to accelerate the proliferation of murine hybridoma B9 cells (Burger et al., *Blood.* 91:1858, 1999; Aoki et al., *Blood* 93:4034, 1999; Jones et al., *Blood* 94:2871, 1999). Thus, the mAbs were cultured with B9 cells in the presence of 100 ng/ml MBPvIL-6. As shown in FIG. 2, the mAbs v6m 12.1.1, (ATTC Deposit No. PTA-2220, deposited in accordance with the Budapest Treaty on Jul. 14, 2000), v6m17.3.2 (ATTC Deposit No. PTA-2217, deposited in accordance with the Budapest Treaty on Jul. 14, 2000), v6m27.1.2 (ATTC Deposit No. PTA-2218, deposited in accordance with the Budapest Treaty on Jul. 14, 2000), and v6m31.2.4 (ATTC Deposit No. PTA-2219, deposited in accordance with the Budapest Treaty on Jul. 14, 2000) demonstrated varying degrees of neutralizing activity against vIL-6 (FIG. 2). The Ab v6m31.2.4 exhibited most prominent neutralizing activity in this bioassay. None of these mAbs suppressed the proliferation of B9 cells in response to hIL-6. The neutralizing activity of anti-vIL-6 mAbs was further confirmed using the SKW6.4 human B cells that are known to produce IgM in response to hIL-6 (Peppard et al., *J Biol. Chem.* 271:7281, 1996). Like hIL-6, MBPvIL-6 dose-dependently stimulated IgM secretion in SKW6.4 cells (FIG. 3A). Maximal production of IgM was obtained with 2 μg/ml of MBPvIL-6 and 5-10 ng/ml of hIL-6. vIL-6-induced IgM production by SKW6.4 cells was suppressed by mAbs v6m12.1.1, v6m17.3.2, v6m27.1.2 and v6m31.2.4 but only minimally by mAbs v6m 13.1.5 or v6m24.2.5 (FIG. 3B). The results of these vIL-6 bioassays indicate that clones v6m12.1.1, v6m17.3.2, v6m27.1.2 and v6m31.2.4 have specific neutralizing activity against vIL-6. Other antibodies, such as polyclonal antibodies that specifically bind the vIL-6 C-terminus (*Science* 274:1739, 1996) did not inhibit B9 cell proliferation. To demonstrate that not all antibodies that bind vIL-6 are neutralizing, COS7 cells were transfected with expression vector pMET7 containing vIL-6 gene or with expression vector pMET7 containing r6-LIv (a reverse control) gene. Serial dilutions of supernatants were incubated in the presence or absence of anti-vIL-6 antiserum generated in rabbits immunized with synthetic peptides of vIL-6 C-terminus (*Science* 274:1739, 1996) with B9 cells (3×10³ cells per well) in a 96-well plate at 37° C. for 72 h, including a 6-h terminal pulse with 1 μCi/well of [³H]-thymidine. [³H]-thymidine incorporation was determined after cell harvesting onto glass fiber filters (see Table 2, below).

TABLE 2

Lack of neutralizing activity of a rabbit polyclonal antibody that binds vIL-6 C-terminal amino acids THYSPPKFDR and PDVTPDVHDR[1]

| Dilution of supernatants | vIL-6 containing supernatant plus anti-vIL6 Ab | | Control supernatant (r60Llv) plus anti-vIL6 Ab | |
|---|---|---|---|---|
| | +[2] | − | +[2] | − |
| 1:2 | 13,653 | 9,057 | 3,002 | 2,853 |
| 1:4 | 8,532 | 7,247 | 1,787 | 1,195 |
| 1:8 | 3,681 | 3,344 | 1,352 | 1,746 |

The results represent mean cpm of triplicate cultures; representative experiments of 5 performed.
[1]Polyclonal antibodies were from Dr. Yuan Chang at Columbia University. These antibodies are generated against synthetic peptides [THYSPPKFDR and PDVTPDVHDR], and are described in U.S. Pat. No. 5,861,500 and in Science 274: 1739, 1996.
[2]Rabbit antiserum against synthetic peptides from vIL-6 amino acid sequences was added at 1:250 dilution.

Thus, previous antibodies known to bind vIL-6 are not neutralizing antibodies.

Example 5

Mapping the Epitopes Recognized by the Neutralizing mAbs

Figure 4:
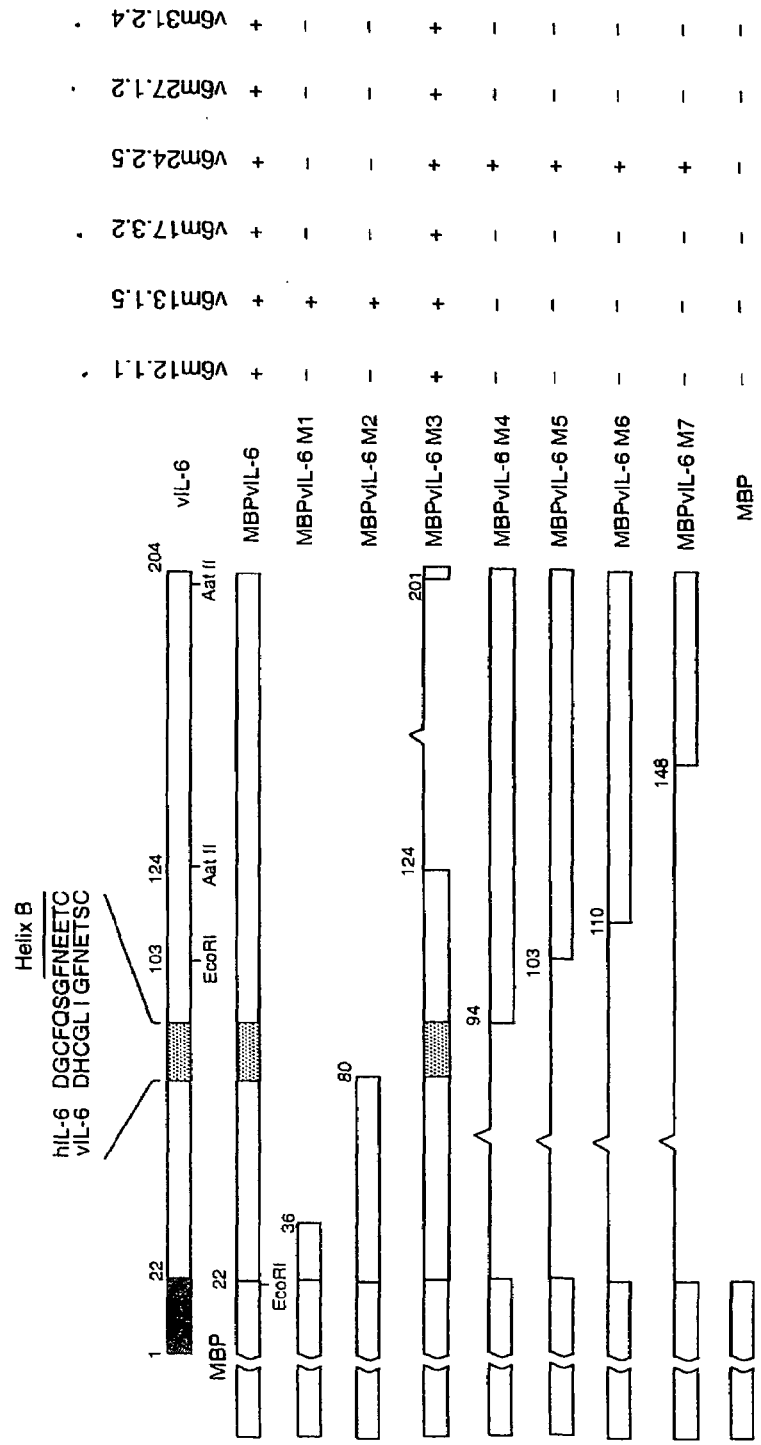
FIG. 4 is a schematic representation of deletion mutants of vIL-6 fusion proteins. Numbers above each box represent the amino acid positions relative to the start methionine. Restriction enzyme sites Aat II and EcoRI used to construct M3 and M5, respectively, are indicated. The reactivity of each monoclonal antibody (mAb) to each fusion protein was determined by ELISA. The reactivity of each mAb to each fusion protein is shown as positive (+) when the absorbance ($A_{405/550}$) was significantly higher (0.7 absorbance units) than the background or negative (–) when the absorbance was similar (within 0.05 absorbance units) to the background. The black box represents the putative vIL-6 signal peptide portion (Neipel et al., *J Virol.* 71:839, 1997). The dotted box denotes 13 amino acids of either a hIL-6 (SEQ ID NO:1) or a vIL-6 fragment (SEQ ID NO:3) that is recognized by 4 neutralizing mAbs against vIL-6. The helix B sequence for hIL-6 (SEQ ID NO:2) and vIL-6 (SEQ ID NO:4) is shown.
Figure 5:
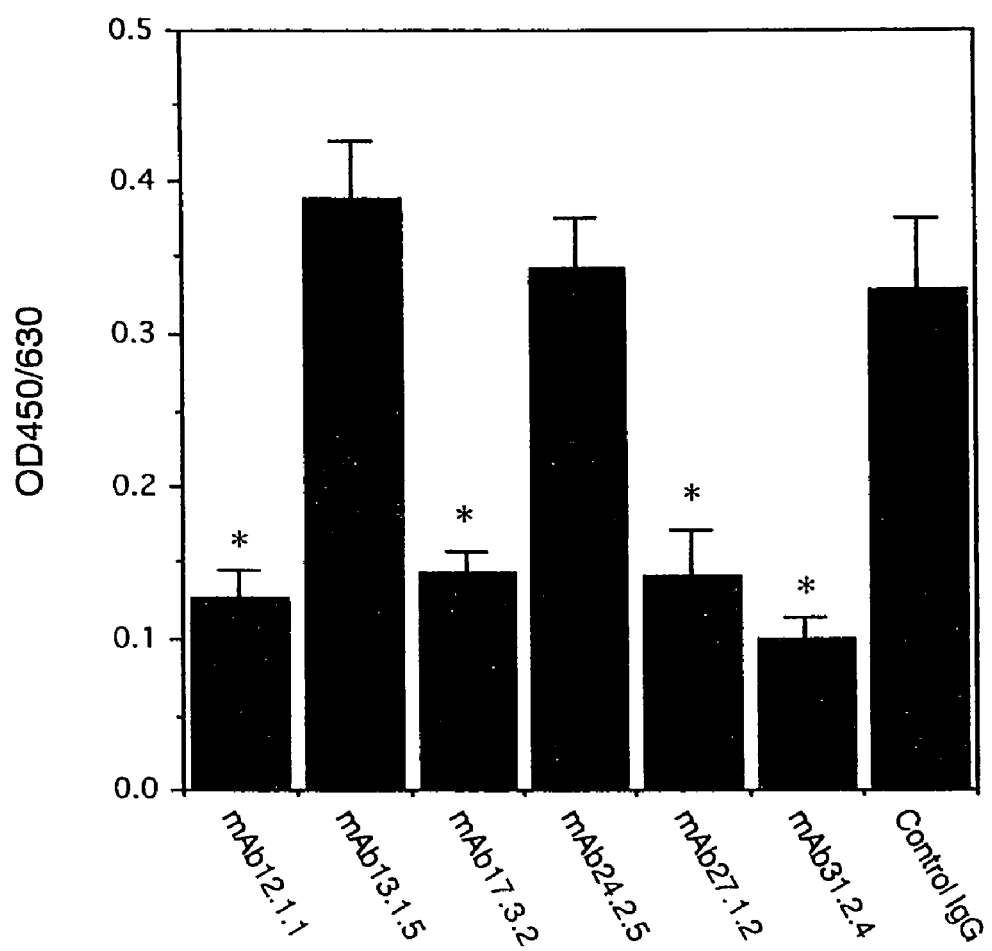
FIG. 5 is a bar graph demonstrating the interference of vIL-6 binding to sgp130 by neutralizing mAbs against vIL-6. Biotinylated MBPvIL-6 (50 ng/ml) was first incubated with anti-vIL-6 mAbs (20 µg/ml) or isotype control mouse IgG1 (20 µg/ml), and then added onto ELISA wells coated with purified sgp130 (2 µg/ml) in triplicates. Bound protein was detected by streptavidin-HRP. The results represent the means±SDs. The asterisk (*) indicates the occurrence of a significant decrease in $OD_{450/630}$ (p<0.002), compared to control Ab. Representative data of two independent experiments are shown.

The antigenic epitopes recognized by v6m12.1.1, v6m17.3.2, v6m27.1.2 and v6m31.2.4 were mapped by ELISA using a panel of MBPvIL-6 fusion proteins (FIG. 4). Plate coating efficiency with fusion proteins was confirmed by reacting with polyclonal anti-MBPvIL-6 Ab. All six Abs similarly recognized full-length vIL-6. The mAb v6m 13.1.5 bound to a 14 amino acid stretch at the N-terminus of vIL-6, and the mAb v6m24.2.5 recognized 5 amino acids at the C-terminus of vIL-6 (FIG. 5). The mAbs v6m12.1.1, v6m17.3.2, v6m27.1.2 and v6m31.2.4 bound to full length MBPvIL-6 and to fragment M3 of MBPvIL-6. This fragment M3, but not other mutants, encompasses an internal 13 amino acids of the vIL-6 fragment at positions 81-93, suggesting that these mAbs map to the vIL-6 fragment inclusive of $Asp^{81}$-$Cys^{93}$. The hIL-6 fragment corresponding to this portion of vIL-6 constitutes the C-terminal part of the AB loop and the beginning of helix B, which are included in the site 1 hIL-6 binding to the IL-6Rα.

Example 6

A Cell-free System to Determine the Interference of vIL-6 Binding to sgp130

KSHV vIL-6 is one of the viral proteins that is implicated in the pathogenesis of AIDS-related malignancies. Although vIL-6 shows multiple biological functions similar to those of cellular IL-6, the usage of IL-6Rs by vIL-6 is still unclear.

Cellular IL-6 exerts its actions through a receptor complex consisting of a specific IL-6-binding protein, IL-6Rα, and a signal-transducing subunit, gp130. The IL-6/IL-6Rα complex induces the homodimerization of two gp130 molecules leading to a number of intracellular signaling events, including activation of the transcription factor NF-IL-6 via activation of the JAK/STAT signaling pathway (Hallek et al., *J Virol.* 73:5149, 1999; Taga and Kisimoto, supra). Cellular IL-6 is unable to transduce signals in the absence of IL-6Rα. Previously, the participation of IL-6Rα in vIL-6 binding cells was deduced from experiments using the IL-6-dependent murine B9 cells (Nicholas et al., *Nat Med.* 3:287, 1997). Supportive evidence for a role of IL-6Rα in vIL-6 function derived from experiments in which neutralization of IL-6Rα abrogated vIL-6-induced HIV-1 p24 production in a human monocytic cell line (Gage et al., *AIDS* 13:1851, 1999). However, other experiments showed that, whereas a combination of anti-IL-6Rα and anti-gp130 Abs blocked the proliferative effect of vIL-6 in the human myeloma INA-6 cell line, anti-IL-6Rα Ab alone did not (Burger et al., *Blood* 91:1858, 1998). In addition, anti-IL-6Rα Ab effectively neutralized the response of HepG2 human hepatoma cells to hIL-6 but failed to block STAT activation by vIL-6 (Molden et al., *J Biol Chem.* 272:19625, 1997). By contrast, anti-gp130 Ab abrogated HepG2 cell signaling in response to both hIL-6 and vIL-6. Moreover, BAF-130 cells, murine pro-B cells expressing transfected human gp130 but not IL-6Rα exhibited a strong response to vIL-6 but not to hIL-6 (Molden et al., *J Biol Chem.* 272:19625, 1997; Mulberg et al., *J Immunol.* 164:4672, 2000). Thus, there seems to be a consensus that gp130 is used for vIL-6 signaling, but the usage of IL-6Rα is subject to controversy.

A cell free system was created in order to examine the ability of the monoclonal antibodies to neutralize vIL-6. This system assessed the biological activity of vIL-6/gp130 binding, described above.

The binding of vIL-6 to gp130 in a cell-free system could be inhibited by neutralizing mAbs to vIL-6. To this end, vIL-6 (50 ng/ml) was first incubated with control mouse IgG1 (20 µg/ml) or anti-vIL-6 mAbs (20 αg/ml) overnight at 4° C., and then tested for binding to sgp130 bound to ELISA plates. Compared with the isotype control murine IgG1, the four anti-vIL-6 neutralizing mAbs interfered with the binding of vIL-6 to sgp130, whereas the two non-neutralizing mAbs did not (FIG. 5). These results strongly support the notion that vIL-6 can exert its bioactivity through direct binding to gp130.

Thus, evidence is provided herein that vIL-6 can bind to sgp130 in the absence of sIL-6Rα in a cell-free system. Neutralizing mAbs directed against vIL-6 interfered with vIL-6 binding to sgp130. These findings strongly support the notion that vIL-6 exerts its biological functions through direct binding to gp130.

The distinct biological activities of the gp130 family of cytokines have been explained by the occurrence of specific receptor chains. Unlike all other members of the IL-6 family, OSM shows a low-affinity binding capacity for gp130, which forms a high-affinity receptor complex with LIFR or OSMR (Tanaka et al., *Blood* 93:804, 1999). OSM transmits a growth-suppressing signal in NIH3T3 cells through a high affinity receptor composed of gp130 and OSMR (Ichihara et al., *Blood.* 90:165, 1997). Although NIH3T3 cells do not express the IL-6Rα and thus do not normally respond to IL-6, IL-6 combined with sIL-6Rα can suppress the growth of NIH3T3 cells (Ichihara et al., *Blood* 90:165, 1997). By contrast, vIL-6 can stimulate NIH3T3 cells to produce vascular endothelial growth factor in the absence of sIL-6Rα (Robledo et al., *Cytokine* 9:666, 1997; Saijonmaa et al., *Am J Physiol.* 275:H662-37, 1998; Bernard et al., *Circ Res.* 85:1124, 1999). These observations have suggested that vIL-6 may exert its biological activities in a fashion similar to OSM. Importantly, OSM is a potent inducer of IL-6 in certain cell types (Wan et al., *J Virol.* 73:8268, 1999; Gage et al., *AIDS* 13:1851, 1999; Kellam et al., *J Virol.* 73:5149, 1999). IL-6 gene expression is regulated by various cis-acting elements, depending upon cell type and nature of the activating agent (Kishimoto et al., *Blood.* 86:1243, 1995). Should vIL-6 be able to induce cells to secrete endogeous IL-6, like OSM, a potential explanation for the contradictory observations about vIL-6 receptor usage would be possible.

Thus, six clones of mAbs were produced against vIL-6. Although the whole molecule of vIL-6 was used for immunization, none of six Abs recognizes cellular IL-6. Of note, even a polyclonal Ab raised in rabbits against vIL-6 failed to recognize hIL-6 and mIL-6. Further, polyclonal anti-mIL-6 Ab that cross-react to hIL-6 did not detect vIL-6.

KSHV vIL-6 shares extensive functional similarity with hIL-6 and mIL-6 although vIL-6 requires up to 1,000-fold larger amounts of protein in bioassays using IL-6 dependent cell lines. Structural differences between vIL-6 and cellular IL-6 and differences in receptor binding affinity may account for the greater amounts of vIL-6 being required for biological activities in vitro.

In the case of vIL-6, it is possible that this viral cytokine can bind to a specific receptor yet to be defined capable of forming functional heterodimers with gp130. Thus, vIL-6, a viral cytokine homologue of a cellular cytokine, appears to share, at least in part, the receptors utilized by the cellular cytokine.

vIL-6 was originally identified in KSHV-positive PEL cells (Moore et al., *Science.* 274:1739, 1996). This viral protein can stimulate the growth of PEL cells in an autocrine/paracrine fashion (Jones et al., *Blood* 94:2871, 1999) and induce vascular endothelial growth factor, which is critical for the growth of PEL and KS in vivo (Aoki et al., *Blood.* 93:4034, 39-43, 1999). Abundant vIL-6 expression has also been detected in the mantle zones of multicentric Castleman's disease (Parravicini et al., *Am J Pathol.* 151:1517, 1997). vIL-6-positive cells in Castleman's disease were negative for CD3, CD20, CD30, CD138, CD45RO, CD68 and EMA. By contrast, hIL-6 is expressed mainly in the germinal centers of Castleman's disease (Yoshizaki et al., *Blood* 74:1360, 1989). Although IL-6Rα is not expressed on resting B cells, vIL-6 could stimulate those cells via direct binding to gp130.

The absence of IL-6Rα expression was previously demonstrated in AIDS-KS cells (Murakami-Mori et al., *J Clin Invest.* 96:1319, 1995), whereas high levels of gp130 expression were noted. OSM, but not IL-6 or LIF, stimulated the growth of AIDS-KS cells, and anti-gp130 Ab completely abolished OSM-induced growth stimulation of AIDS-KS cells (Murakami-Mori et al., *J Clin Invest.* 96:1319, 1995). A proportion of HIV-positive patients have detectable vIL-6 in sera and body fluids (Aoki et al. manuscripts in press and submitted), which may promote the development of AIDS-associated malignancies by constitutive phosphorylation of gp130 or by inducing vascular endothelial growth factor. Deregulation of cellular IL-6 expression is known to contribute to tumor development, suggesting that KSHV-derived vIL-6 could be part of a viral strategy to promote malignant transformation. Neutralizing activity of anti-vIL-6 Abs may provide a new experimental therapeutic for KSHV-associated disorders.

Example 7

Gp130 Binding Surfaces are not Fully Shared by Human and vIL-6

Figure 11:
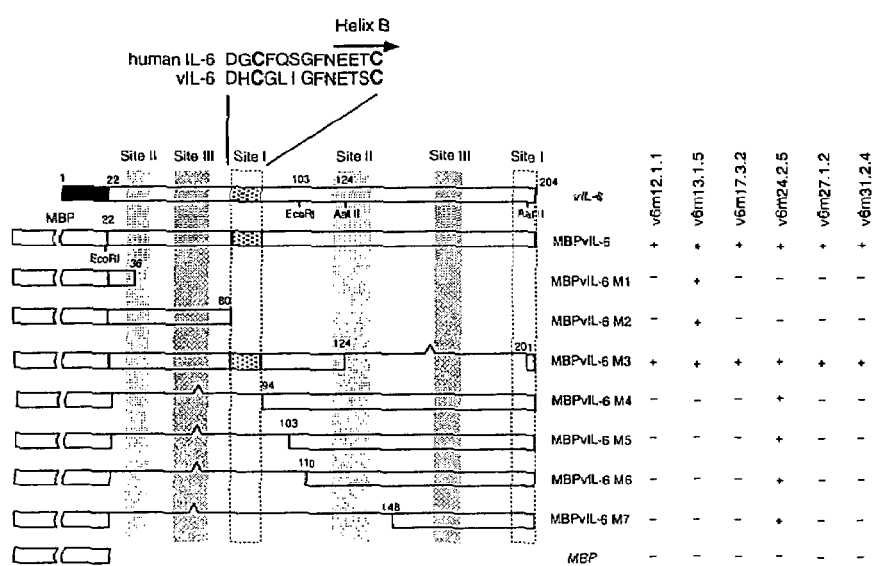
FIG. 11 is a schematic diagram of fusion protein mapping of anti-vIL-6 mAbs. Schematic representation of deletion mutants of vIL-6 fusion proteins. Numbers above each box represent the amino acid positions relative to the start methionine. Restriction enzyme sites Aat II and EcoRI used to construct M3 and M5, respectively, are indicated. The reactivity of each mAbs to each fusion protein was determined by ELISA. The reactivity of each mAb to each fusion protein is shown as positive (+) when the absorbance ($A_{405/550}$) was significantly higher (0.7 absorbance units) than the background or negative (–) when the absorbance was similar (within 0.05 absorbance units) to the background. The black box represents the putative vIL-6 signal peptide portion (Neipel et al., *J Virol* 1997; 71:839-842). The dotted box denotes a 13 aa peptide of vIL-6 that is recognized by 4 neutralizing mAbs against vIL-6. The bold characters indicate the second conserved cysteine residues. vIL-6 sites I, II and III are defined based on the crystal structure of the vIL-6/gp130 complex (Chow et al., *Science* 2001; 291:2150-2155).

It was examined if the vIL-6 epitope that the neutralizing mAbs recognize is used as a direct binding surface for gp130. Murine IL-6 is species-specific whereas human IL-6 binds to both human and murine receptors. To exclude a potential contribution of vIL-6-induced cellular IL-6, murine BAF-B03 cells stably transfected with human gp130 were utilized. This cell line is known to respond to vIL-6 but not to human IL-6 in the absence of sIL-6R (Molden et al., *J Biol Chem* 1997; 272:19625-19631; Narazaki et al., *Blood* 1993; 82:1120-1126). As expected, human IL-6/sIL-6R induced DNA synthesis in BAF-130 cells. In agreement with its lower binding affinity, vIL-6 had much lower specific activity than human IL-6/sIL-6R. The vIL-6 deletion mutant MBPvIL-6 M3, which contains the region of $Asp^{81}$-$Cys^{93}$ within site I but lacks full site II and III comprising the reported vIL-6 interface with gp130 (FIGS. 9 and 11), did not induce DNA synthesis in BAF-130 cells or compete for vIL-6 or human IL-6/sIL-6R binding to gp130. This suggested either that this vIL-6 epitope is not part of the vIL-6 binding surface to gp130, as shown by the vIL-6 crystal structure, or that this fragment alone is not sufficient for biological activity. Neither parental BAF-B03 cells nor mock transfectants responded to vIL-6.

It was then examined if human and vIL-6 share the same gp130 binding sites using a panel of anti-gp130 mAbs. These Abs are known to recognize specific functional sites of gp130 for signal transduction by IL-6-type cytokines (Wijdenes et al., *Eur J Immunol* 1995; 25:3474-3481; Muller-Newen et al., *J Biol Chem* 2000; 275:4579-4586). As reported previously, all three anti-gp130 mAbs B-R3, B-P4 and B-P8, but not an isotype control, inhibited human IL-6-induced DNA synthesis in BAF-130 cells. By contrast, when stimulated with vIL-6, mAbs B-R3 and B-P4, but not B-P8, suppressed DNA synthesis in BAF-130 cells (Muller-Newen et al., *J Biol Chem* 2000; 275:4579-4586; Kurth et al., *J Immunol* 2000; 164:273-282). The mAb B-P4 recognizes the membrane-proximal extracellular part of gp130 (D4D5D6) that is critical for homodimerization of gp130 (Kurth et al., *J Immunol* 2000; 164:273-282). The B-R3 mAb interferes with gp130 binding by all IL-6-family cytokines, whereas B-P8 mAb interferes with gp130 binding by human IL-6 and ciliary neurotrophic factor(Wijdenes et al., *Eur J Immunol* 1995; 25:3474-3481; Kurth et al., *J Immunol* 2000; 164:273-282). The mAbs B-R3 and B-P8 recognize the epitopes in gp130 D2 and D3, respectively, which constitute the cytokine binding module (Wijdenes et al., *Eur J Immunol* 1995; 25:3474-3481; Muller-Newen et al., *J Biol Chem* 2000; 275:4579-4586). These results provide evidence that human and vIL-6 share an epitope in D2 of gp130, and that both cytokines induce homodimerization of gp130. In addition, the result show that vIL-6 does not bind to the epitope in gp130 D3 which is critical to human IL-6 function.

vIL-6 shows biological functions similar to those of cellular IL-6, however, based on the interaction between vIL-6 and its receptor(s) appears to be different. Evidence is provided herein that vIL-6 does not bind to IL-6R in a cell-free system. By both surface plasmon resonance and/or ELISA, vIL-6 bound gp130 without a need for IL-6R and failed to bind IL-6R. In addition, mAb v6m24.2.5 recognizing the C-terminal end of helix-D of vIL-6 did not show neutralizing activity in bioassays. In contrast to these results with vIL-6, the corresponding C-terminal end of helix-D in human IL-6 is included in the binding face to IL-6R, and the binding of mAb to this region totally abrogated human IL-6 activity by blocking the ligand interaction to IL-6R (Brakenhoff et al., *J Immunol* 1990; 145:561-568).

Figure 9:
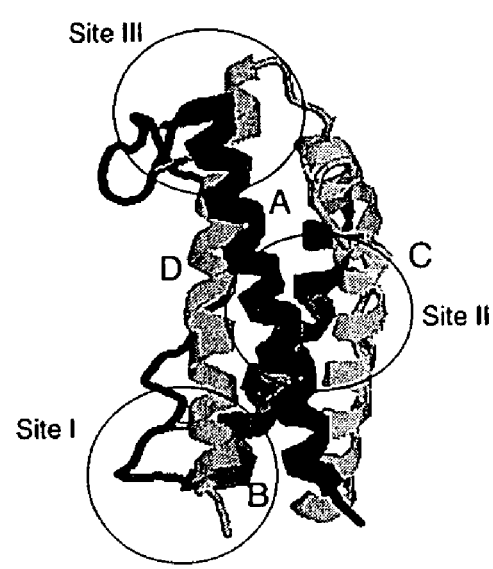
FIG. 9 is a set of schematic representations of vIL-6 structure.
Figure 9:
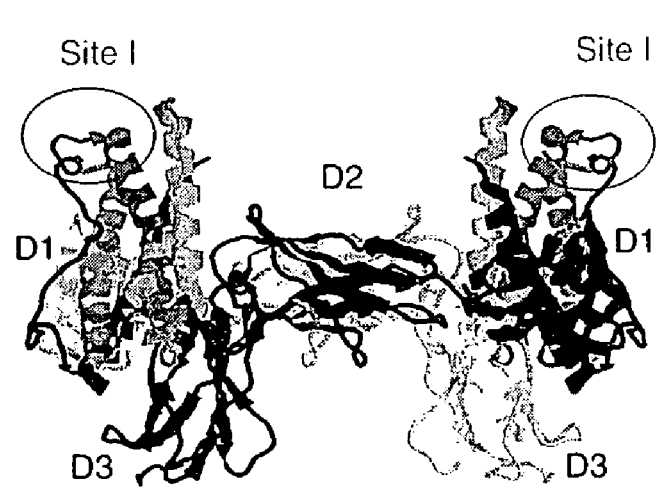

Using the structure of the growth hormone/growth hormone receptor complex as a paradigm for cytokine receptor complex assembly, IL-6-type cytokines are believed to have three topologically discrete sites of interactions with their receptors (FIG. 9). Site I, if used, is always engaged by a non-signaling receptor: IL-6R, IL-11R or ciliary neurotrophic factor receptor. Site II is always engaged by gp130, and site III by a second signaling receptor gp130, OSMR or LIFR (Bravo et al., *EMBO J* 2000; 19:2399-2411). Within gp130, three binding epitopes have been identified as critical to its activation by human IL-6/IL-6R: one epitope involves the Ig-like domain (D1); another epitope is located in the cytokine binding module (D2D3); and the other is located in the membrane-proximal extracellular domains (D4D5D6) (Kurth et al., *J Immunol* 2000; 164:273-282). According to the crystallographic analysis of the vIL-6/sgp130 (D1D2D3) complex (Chow et al., *Science* 2001; 291:2150-2155), sequence alignment of human and vIL-6 shows that contact residues seen in the structure of the vIL-6/gp130 complex are in the same positions as human IL-6-gp130 contact residues previously mapped by mutagenesis (Simpson et al., *Protein Sci* 1997; 6:929-955). In cell culture, the membrane-proximal extracellular part of gp130 (D4D5D6) is critical for vIL-6 mediated-signaling, even though vIL-6 can form a tetrameric complex with gp130 (D1D2D3) (Chow et al., *Science* 2001; 291:2150-2155). Further, although human and vIL-6 share an epitope in gp130 D2, vIL-6 does not appear to utilize an epitope in gp130 D3 that is critical to human IL-6 function. Together with the evidence that vIL-6 does not bind IL-6R.

In the studies described herein, the neutralizing mAbs directed against vIL-6 recognize a region of the C-terminal part of the AB-loop and the beginning of helix-B. The binding of mAb to this region can change the mobility of helix-B and interfere with the ability of site II and III to achieve a proper orientation. Without being bound by theory, the binding of human IL-6 to IL-6R could modify a loop-helix interaction into active conformation before binding to gp130. In the case of vIL-6, the absence of a specific receptor chain may result in the low binding affinity of vIL-6 to gp130 by failure to be locked in a high affinity conformation.

Example 8

Use of a vIL-6 Specific Binding Agent to Diagnose PEL: Materials and Methods Primary effusion lymphoma (PEL) is a peculiar and infrequent type of non-Hodgkin's lymphoma that arises predominantly in human immunodeficiency virus (HIV)-infected individuals. PEL displays liquid growth in the serous cavities of the body, often in the absence of a clearly identifiable tumor mass (Cesarman et al., *Semin Cancer Biol* 9:165-174, 1999). In most cases, PEL cells are dually infected with Epstein-Barr virus and Kaposi's sarcoma-associated herpesvirus (KSHV; also known as human herpesvirus 8) (Nador et al. *Blood* 88:645-656, 1996; Gaidano et al., *Blood* 90:4894-4900, 1997), and produce several cytokines, including a viral homologue of interleukin (IL)-6

(vIL-6) (Moore et al., *Science* 274:1739-1744, 1996; Nicholas et al., *Nat'l Med* 3:287-292, 1997; Neipel et al, *J Virol* 71:839-842, 1997).

Although HIV-associated lymphomagenesis is poorly understood, experiments in vitro and transgenic models have shown that HIV-derived proteins can activate a number of cellular genes. For example, the HIV transactivator protein Tat has been reported to promote expression of hIL-6 and hIL-10 in lymphoid cells (Kundu et al., *Blood* 94:275-282, 1999). Further, HIV infection and soluble factors released from HIV-infected cells can induce lytic replication of KSHV in a PEL cell line (Varthakavi et al., *J Virol* 73:10329-10338, 1999). hIL-6 expression, which is constitutive in PEL cell lines, is downregulated during KSHV lytic replication induced by phobor esters (Asou et al., *Blood* 91:2475-2481, 1998). By contrast, vIL-6 expression, which is low in PEL cell lines latently infected with KSHV, is markedly induced during KSHV lytic replication (Sarid et al., *J Virol.* 72(2):1005-1012, 1998). The potential relationships between HIV load and the induction of selected cellular and KSHV-derived cytokines was investigated.

In order to evaluate the role of vIL-6 in PEL, the following materials and methods were used:

Patients: Body cavity effusions from 8 AIDS patients with PEL, 21 HIV-negative patients with malignancies or congestive heart failure, and 4 AIDS patients with inflammatory processes without PEL were obtained from the AIDS Malignancy Bank (National Cancer Institute, Bethesda, Md.) and from our Institutes. The diagnosis of PEL was based on clinical presentation, histology of the effusion cells, and the presence of KSHV in the lymphoma cells. HIV-RNA load was measured by standard techniques.

Enzyme-Linked Immunosorbent Assays (ELISA) for vIL-6, hIL-6 and hIL-10: The ELISA for vIL-6 utilized a mouse monoclonal and rabbit polyclonal antibodies raised against recombinant vIL-6 (Jones et al., *Blood* 94:2871-2879, 1999; Aoki et al., *Blood* 93:4034-4043, 1999; Aoki et al., *Blood* 94:431a, 1999). Polystyrene plates (Immunol 1B; Dynex Technologies, Chantilly, Va.) were coated with mouse monoclonal anti-vIL-6 antibody (v6m12.1.1; 4 µg/ml in carbonate buffer, pH 9) overnight at 4° C. After washing the plates with PBS containing 0.05% Tween 20 (PBS-T) and blocking with SuperBlock (Pierce, Rockford, Ill.), test samples were added in triplicate to the wells (initial dilution 1:10 in PBS-T). Plates were incubated overnight at room temperature, and washed with PBS-T. Rabbit polyclonal anti-vIL-6 antibody (0.5 µg/ml) was added to the wells in PBS-T containing 0.5% bovine serum albumin (PBS-T/BSA). Plates were incubated for 2 h at room temperature and washed. Affinity-purified, human serum protein absorbed goat anti-rabbit IgG antibody conjugated to alkaline phosphatase (Sigma, St. Louis, Mo.; 1:400 dilution in PBS-T/BSA) was added. Plates were incubated at room temperature for 1.5 hours, washed with PBS-T, p-nitrophenolphosphate substrate (Sigma) added to the wells, and plates were read at 405 nm with λ correction at 595 nm. A purified fusion protein of maltose-binding protein (MBP: 42.7 Kd) and amino acids 22-204 of vIL-6 (21.6 Kd) was used as the standard (Aoki et al., *Blood* 93:4034-4043, 1999). The concentration of vIL-6 was calculated from absorbance values in relation to the standard curve, correcting for the presence of the MBP fusion protein in the vIL-6 standard (vIL-6 corresponds to 33.6% of MBPvIL-6). hIL-6 and hIL-10 were measured by commercially available ELISA kits (R & D Systems, Minneapolis, Minn.).

Western Blotting: Western blotting for vIL-6 and hIL-6 was performed as described previously (Aoki et al., *Blood* 93:4034-4043, 1999). Rabbit polyclonal and a mouse monoclonal (v6m 12.1.1, see above) antibodies against vIL-6, and mouse monoclonal antibody against hIL-6 (MAb206; R&D Systems) were used as the primary antibodies. MBPvIL-6 was cleaved with factor Xa (New England BioLabs, Beverly, Mass.).

Statistical Analysis: The non-parametric Spearman-Rho test was used to measure the significance of correlations between groups.

Example 9

Use of a vIL-6 Specific Binding Agent to Detect PEL: Results vIL-6 exhibits 24.7% amino acid identity to hIL-6 (Moore et al., *Science* 274:1739-1744, 1996). Thus, an assay for vIL-6 must be able to distinguish it from hIL-6. As assessed by both immunoblotting and direct ELISA, neither a rabbit polyclonal nor a mouse monoclonal antibodies raised against recombinant vIL-6 recognize hIL-6. Using these antibodies, a vIL-6 ELISA was developed. This assay displays a lower limit of sensitivity calculated at approximately 30 pg/mL of vIL-6, and is linear between 30 and 3,360 pg/mL of vIL-6. This ELISA does not detect hIL-6 (FIG. 6A), and a commercial hIL-6 ELISA kit (R&D Systems) does not detect vIL-6 (FIG. 6B).

PEL cell cultures consist largely of cells latently infected with KSHV, with a minority of cells undergoing lytic KSHV replication (Renne et al., *Nat Med* 2:342-6, 1996). Treatment with the phorbol ester 12-O-tetradecanoylphorbol-13-acetate (TPA) rapidly induces lytic KSHV replication. The KSHV-positive PEL cell lines BC-1, BCP-1, and BCBL-1 were found to release vIL-6 into the supernatant, as did the vIL-6 transfected NIH3T3 v6O cells (Table 3) (Aoki et al., *Blood* 93:4034-4043, 1999).

TABLE 3

Detection of vIL-6 in the culture supernatants of cell lines [1]

| cell line | culture without TPA (vIL-6 pg/mL) | culture with TPA (vIL-6 pg/mL) |
|---|---|---|
| BC-1 [2, 3] | 2880 | 26300 |
| BCP-1 [2] | 19200 | 118100 |
| BCBL-1 [2] | 1680 | 29100 |
| Daudi [3] | <30 | <30 |
| v6O [4] | 88600 | ND |
| VDS-O1 [3, 5] | <30 | ND |

[1] To prepare conditioned media, suspension cells were seeded in 12-well plates at 1 × 10$^6$ cells/well in 2.5 ml of RPMI1640 medium supplemented with 10% fetal bovine serum and cultured with or without 20 ng/mL TPA (Sigma) for 48 hours. Adherent cells were seeded in 6-well plates at 1 × 10$^6$ cells/well in 2.5 ml culture media, and cultured for 48 hours. The concentration of fetal bovine serum in each supernatant was adjusted to be 10%. Data represent the mean of duplicate assays.
[2] KSHV-positive cell lines (Moore et al.,. Science 274: 1739-1744, 1996; Renne et al., Nat Med 2: 342-6, 1996; Cesarman et al., Blood 86: 2708-2714, 1995).
[3] EBV-positive cell lines (Aoki et al., Blood 94: 4247-4254, 1999).
[4] NIH3T3 cells stably transfected with vIL-6-expression vector (Aoki et al., Blood 93: 4034-4043, 1999).
[5] Lymphoblastoid cells stably transfected with hIL-6-expression vector. (Tanner et al., J Clin Invest 88: 239-247, 1991).
ND: not determined.

Addition of TPA to PEL cells enhanced vIL-6 release in the culture supernatants. No vIL-6 was detected in the supernatants from the KSHV-negative Burkitt's lymphoma cell line Daudi or the EBV-immortalized VDS-O1 cell line which is transfected with a hIL-6 expression vector (Tanner et al., *J Clin Invest* 88:239-247, 1991.

vIL-6 was detected in 6 of 8 PEL effusions (mean 13,884 pg/mL), but was undetectable in the 21 control benign or malignant effusions from HIV-negative individuals (not shown; p<0.0001, Fisher's Exact test). vIL-6 was also undetectable in 4 non-malignant effusions from patients with AIDS (not shown). HIV RNA was examined in 8 malignant lymphomatous effusions (Table 4).

TABLE 4

HIV load and cytokines in AIDS-PEL effusions

| case | HIV RNA copies/mL[1] | vIL-6 (pg/mL)[2] | hIL-6 (pg/mL)[3] | hIL-10 (pg/mL)[3] |
|---|---|---|---|---|
| 1 | 59796 | 66630 | 6787 | 87222 |
| 2 | inhibitory[4] | 9670 | 15561 | 231454 |
| 3 | >750000 | <300 | 957 | 2521297 |
| 4 | 8741 | <300 | 37494 | <8 |
| 5 | 66353 | 1390 | 6856 | 66 |
| 6 | 111920 | 16350 | 4935 | 103414 |
| 7 | 2169 | 10120 | 8395 | 8327 |
| 8 | 88801 | 6913 | 15097 | 1342318 |

[1]HIV-RNA was measured by quantitative RT-PCR kit (Roche Amplicor HIV-test).
[2]Due to the initial 1:10 sample dilution, the lower limit of ELISA sensitivity was set at 300 pg/mL of vIL-6.
[3]Data represent the mean of triplicate assays.
[4]Test results indicated the presence of an inhibitor of RT-PCR in this sample.

Except for one sample where test results could not be evaluated because of an inhibitor, HIV RNA was detected in all PEL effusions (mean 562967 copies/mL). hIL-6 was detected in all AIDS-PEL effusions (mean 12010 pg/mL) and in all control HIV-negitive effusions (mean 41,737 pg/mL; range 127-624,870 pg/mL). No significant correlation was observed between vIL-6 and hIL-6 levels in PEL effusion (r=−0.2275; p=0.5878). hIL-10 was detected in 7 of 8 PEL effusions (mean 536,762 pg/mL). A statistically significant association was observed between HIV load and hIL-10 levels (r=0.7857; p=0.0362). However, no significant association was noted between HIV load and vIL-6 (r=−0.1622; p=0.7283) and hIL-6 levels (r=−0.6786; p=0.0938).

Thus, PEL effusions generally contain vIL-6, hIL-6, hIL-10 and HIV RNA. These PEL effusions contain high levels of VEGF (mean 3,977 pg/mL; range 1,133-11,417 pg/ml) (Aoki et al., Blood 95:1109-1110, 2000). PEL cells are a likely source of vIL-6, hIL-6, hIL-10 and VEGF detected in the lymphomatous effusions because PEL cell lines can express all these proteins in culture (Jones et al., Blood 94:2871-2879, 1999; Aoki et al., Blood 94:4247-4254. 1999). VEGF, which stimulates vascular permeability and may facilitate the accumulation of PEL effusions in vivo, was required for a PEL cell line to form effusion lymphomas in mice (Aoki et al., Blood 94:4247-4254. 1999). hIL-6 and vIL-6, individually, can stimulate the expression of VEGF in tissues. In vitro, hIL-10 and vIL-6 serve as autocrine growth factors for PEL cell lines (Jones et al., Blood 94:2871-2879, 1999), and may promote PEL cell growth in the body cavities. The observation that PEL effusions generally contain vIL-6 which can stimulate PEL cell growth and promote the accumulation of effusions further suggests that this vIL-6 plays a critical role in PEL pathogenesis.

Example 10

Detection of vIL-6 in Castleman's Disease

A 40-year-old HIV-positive homosexual man presented with a sore throat, non-productive cough, night sweats, fever, diarrhea, marked fatigue and weight loss. The patient had received highly active antiretroviral therapy (HAART) for three years, including lamivudine (3TC: 150 mg twice per day), stavudine (d4T: 40 mg twice per day) and nelfinavir (NFV: 2250 mg per day). HIV load had been stable at less than 1,200 copies/mL since 1996. CD4+ T-cell counts had remained over 300 cells/mm (Aoki et al., manuscript submitted). On physical examination, the patient had lymphadenopathy, abdominal distention with hepatosplenomegaly, abdominal tenderness and skin rash but no evidence of Kaposi's sarcoma. Oral administration of prednisone (30 mg of per day) was started to relieve systemic inflammatory symptoms. A cervical lymph node biopsy displayed abnormal histology that shows the typical features of mixed plasma cell/hyaline vascular type of multicentric Castleman's disease (Oksenhendler et al., AIDS 10:61-7, 1996). The lymph node displayed concentric layers of small lymphocytes surrounding the germinal centers and plasma cells infiltration in the interfollicular areas. Due to a dramatic improvement of systemic symptoms, prednisone was tapered after 10 days, and administration of Foscamet (7 g twice per day), an anti-herpesvirus agent, started. The patient was splenectomized in September, 1999, and has been well for nine months. No serum samples have been available for analysis since August, 1999.

The serum samples were analyzed retrospectively. vIL-6 was measured by a vIL-6-specific (does not recognize hIL-6) ELISA established in our laboratory (see above). hIL-6 was measured by a commercially available ELISA kit (R&D Systems, Minneapolis, Minn.) which does not detect vIL-6.

The presence of the KSHV antigens was examined in tissues by immunohistochemistry using monoclonal antibodies against latency-associated nuclear antigen LANA (Dupin et al., Proc Natl Acad Sci USA. 96:4546-51, 1999) and vIL-6 (as described herein), according to previously described methods (e.g. see Aoki et al., Blood. 93:4034-4043, 1999). Immunohistochemical staining of the lymph node for hIL-6 was performed using monoclonal antibodies against hIL-6 (MAB206; R & D systems). HIV-RNA load was measured by standard techniques.

Figure 7:
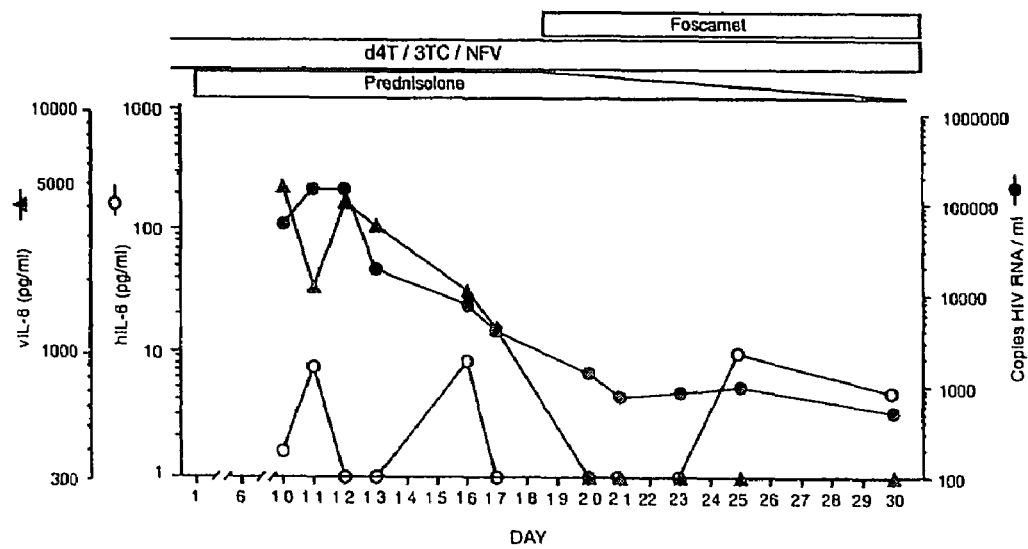
FIG. 7 is a graph showing the detection of vIL-6, hIL-6 and HIV RNA in serial serum samples from an HIV-positive patient with Castleman's disease. Day 1 denotes the day in which prednisone treatment was initiated. The lower limit of ELISA sensitivity in serum was calculated to be 300 pg/mL of vIL-6 and 1.0 pg/mL of hIL-6. 3TC: lamivudine; d4T: stavudine; NFV: nelfinavir.

KSHV infection in the patient was confirmed by the immunochemical detection of the KSHV nuclear antigen LANA in a lymph node biopsy specimen. A vIL-6 specific monoclonal antibody detected expression of vIL-6 in the same lymph node specimen by immunohistochemistry. The KSHV-LANA positive and vIL-6 positive cells localized predominantly to the mantle zone of the lymph node with similar proportion. By contrast, expression of hIL-6, which has previously been detected in the germinal centers of certain Castleman's disease cases, was not detectable by immunohistochemistry in this lymph node. The vIL-6, hIL-6 and HIV-RNA load in the patient's serum was measured at various time intervals, beginning 10 days after initiation of steroid treatment (FIG. 7). Serum vIL-6 was initially detected at 4,756 pg/mL. However, vIL-6 decreased to undetectable (less than 300 pg/mL) levels over the next 10 days and subsequently remained undetectable. The HIV RNA load also presented remarkable changes during this period. For approximately 3 years prior to the onset of Castleman's disease, the HIV RNA load in this patient had remained at less than 400 copies/mL. No serum samples were available from these years for vIL-6 measurement. After Castleman's disease was diagnosed, the HIV RNA load peaked at 146,460 copies/m, followed by a rapid decrease to 792 copies/mL on day 21 of treatment (FIG. 7). Of note, the patient continued to receive the same antiretroviral drug regimen he had received during the previous 3 years. Thus, vIL-6 and HIV RNA serum levels displayed parallel decreases over a 20 day period of observation following initiation of steroid treatment for multicentric Castleman's disease (r=0.882: p=0.0053, Spearman Rho test). By contrast, serum levels of hIL-6 fluctuated at low levels (range<1.0-10.8 pg/mL) throughout this period.

Deregulation of hIL-6 has been previously implicated in the pathogenesis of Castleman's disease. The germinal centers of hyperplastic lymph nodes in multicentric Castleman's disease were reported to express abundant hIL-6, and serum levels of hIL-6 were found to be abnormally elevated (Parravicini et al., *Am J Pathol.*151:1517-22, 1997; Beck et al., *N Engl J Med.* 330:602-5, 1994). In selected patients with Castleman's disease, neutralizing antibodies against human (non-viral) IL-6 may have exerted a therapeutic effect (Beck et al., *op. cit.*). In contrast to hIL-6, the role of KSHV-encoded vIL-6 in Castleman's disease is unclear. Virtually all HIV-positive cases of multicentric Castleman's disease and nearly 50% of HIV-negative cases are infected with KSHV (e.g. see Soulier et al. *Blood* 86:1276-80, 1995) and all KSHV-positive Castleman's disease tissues were found to express vIL-6 (Parravicini, supra). Studies in mice suggested that vIL-6 may directly stimulate B cell proliferation and differentiation suggesting its potential role in the pathogenesis of multicentric Castleman's disease (Nicholas et al., *Nat Med.* 3:287-92, 1997). In addition, since vIL-6 can induce vascular endothelial growth factor, a potent angiogenic factor, vIL-6 could indirectly contribute to increased lymphatic angiogenesis that is often noted in Castleman's disease lesions. The results described herein demonstrated that vIL-6 was detected in the circulation of an AIDS patient with multicentric Castleman's disease, but became undetectable soon after initiation of steroid treatment that resulted in clinical remission.

Recent studies have focused on the relationship between HIV and KSHV infection. Some experiments in vitro have shown that vIL-6 can activate HIV-1 replication in human monocytes (Gage et al., *AIDS* 13:1851-5, 1999), others that HIV infection and soluble factors released from HIV-infected cells can induce lytic KSHV replication in a PEL cell line (Varthakavi et al., *J Virol.* 73:10329-38, 1999). In the patient described herein, the onset of multicentric Castleman's disease was associated with a marked increase of the HIV RNA load followed by a rapid return to lower levels. The anti-retroviral therapy had not changed in this patient so it is unlikely that either the increase or the decrease in HIV-RNA load is attributable to this therapy. HIV-1 is not known to infect B cells in Castleman's disease lesions, so that it is unlikely that tumor burden per se is responsible for the increase in HIV-RNA load. Rather, it is more likely that factors derived from Castleman's disease lesions, including vIL-6, may have activated HIV replication in this patient.

Initiation of steroid treatment was associated with a rapid antitumor response, a decrease in the patient's HIV RNA load and a parallel decrease of vIL-6 serum levels. This outcome is consistent with the notion that the reduction of Castleman's disease burden induced by steroids also reduced factors derived from these tissues, including vIL-6. In turn, reduction of vIL-6, and perhaps other factors derived from Castleman's disease tissues, may have removed a signal for HIV replication, and allowed HIV RNA load to return to levels measured prior to the onset of Castleman's disease. While the factors contributing to the onset of multicentric Castleman's disease are likely multiple, the remarkable association between circulating vIL-6 levels and Castleman's disease status shown here, combined with previous information on the biological activities of this cytokine, supports a role of vIL-6 in the pathogenesis of this lymphoproliferative disorder. Administration of a specific binding agent which neutralizes a biological activity of vIL-6 can thus be utilized to treat Castleman's disease (see Example 11, below).

Example 11

Detection of Kaposi's Sarcoma-associated Herpesvirus (KSHV)-encoded Interleukin-6 in KSHV-related Disorders Methods:

Patients and Blood Donors: Sera from healthy controls, HIV-positive individuals, and patients with KS, PEL or MCD were collected from blood banks and clinical centers located in the United States. Samples were stored at −70° C. prior to testing. RNA load of HIV was determined by standard techniques. Counts for CD4 or CD8 positive cells were determined by flow cytometry.

ELISA for viral and human IL-6: An ELISA for vIL-6 was performed as described herein. Briefly, polystyrene plates (Immunol 1B; Dynex Technologies, Chantilly, Va.) were coated with mouse monoclonal anti-vIL-6 antibody (v6m 12.1.1; 4 µg/mL in carbonate buffer, pH 9). After washing the plates with PBS containing 0.05% Tween 20 (PBS-T) and blocking with SuperBlock (Pierce, Rockford, Ill.), test samples were added in triplicate to the wells (initial dilution 1:10 in PBS-T). Plates were incubated overnight, washed with PBS-T, and rabbit polyclonal anti-vIL-6 antibodies (0.5 µg/mL) were added to the wells in PBS-T containing 0.5% bovine serum albumin (PBS-T/BSA). Plates were incubated for 2 h, washed, and affinity-purified, human serum protein absorbed goat anti-rabbit IgG antibody conjugated to alkaline phosphatase (Sigma, St. Lois, Mo.; 1:400 dilution in PBS-T/BSA) was added. Plates were incubated for 1.5 hours, washed, and p-nitrophenolphosphate substrate (Sigma) added to the wells. The absorbance values were read at 405 nm with λ correction at 595 nm. A purified preparation of *E. coli*-derived recombinant vIL-6 was used as the standard. The concentration of vIL-6 was calculated from absorbance values in relation to the standard curve. Quantification of human IL-6 was performed using a human IL-6 Quantikine kit (R & D, Minneapolis, Minn.) that does not detect vIL-6.

Statistical Analysis: The Fisher's Exact test was used to examine the relationship between vIL-6 and sex, HIV risk factors, distribution of KS, lymphadenopathy, use of anti-herpesvirus agents and use of anti-retroviral agents. Mann-Whitney U test was used to examine the relation between seroprevalence of vIL-6 and HIV load, counts of $CD4^+$ T cells, $CD8^+$ T cells, and platelets.

Figure 8:
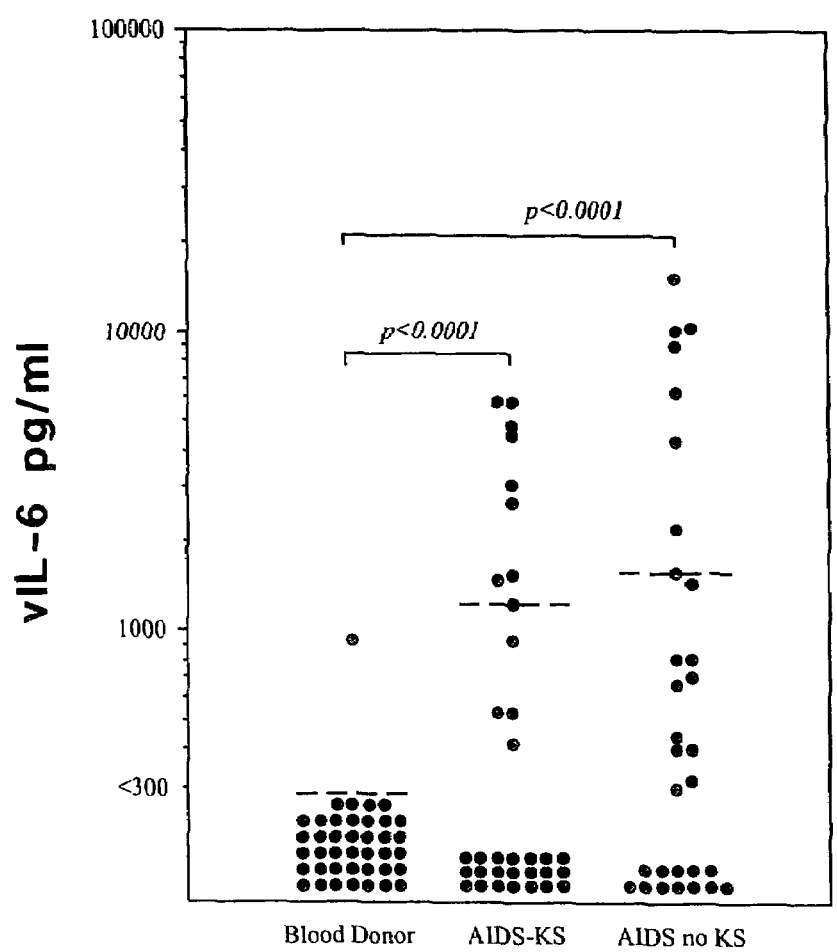
FIG. 8 is a chart documenting the detection of vIL-6 in sera from normal blood donors, HIV-positive patients with or without KS, and patients with classic KS. The lower limit of ELISA sensitivity in serum samples was set at 300 pg/mL of vIL-6.

Results: As described above, a vIL-6-specific ELISA that does not detect human IL-6 has been developed. The lower limit of assay sensitivity was determined to be 30 pg/ml of vIL-6. Serum samples were run at an initial 1:10 dilution, and the lower limit of ELISA sensitivity for serum was thus set at 300 pg/ml. vIL-6 was measurable in 1 of 40 blood donors (FIG. 8). To test for false positive ELISA reactions, we repeated the assays without coating the plates with capture monoclonal antibody against vIL-6. Both previously positive samples were negative in the absence of coating, providing evidence that positive reactions were not attributable to nonspecific binding of the detection antibodies or substrate.

The vIL-6 levels in serum from patients with AIDS-associated KS was measured (FIG. 8). vIL-6 was detectable in serum from 16 of 34 patients (45.7%; range 370-7,460 pg/mL). To better evaluate the results of vIL-6 testing in patients with AIDS KS, serum vIL-6 was measured in a group of 30 HIV-positive individuals without KS, PEL or MCD. Most (90.6%) of these HIV-positive individuals were homosexual males who met the diagnostic criteria of AIDS. vIL-6 was detected in 19 of these 30 HIV-positive individuals without evidence of KSHV-related diseases (65.5%; range 301-15,060 pg/mL). Thus, the serum levels of vIL-6 in the HIV-positive patients with KS and those without KS, PEL or MCD were similar (p=0.1846).

In 10 of the HIV-positive patients without KS, PEL or MCD, serum samples were obtained at more than one time. Thus, vIL-6 was measured in all available serum sample from these patients (Table 5).

The serum levels of human IL-6 were also measured, and information was collected on multiple disease-related factors such as HIV-RNA load, CD4+ and CD8+ cell counts, and treatment for HIV and herpes virus (Table 4). Serum levels of vIL-6 levels generally remained stable over a period of months as did the HIV RNA load on anti-retroviral treatment, whereas CD4 cell counts fluctuated. Human IL-6 was either undetectable or detected at low levels (<1.0-116 pg/mL; median 2.4 pg/mL) in all sera. In this small group, no clear association was noted between serum levels of vIL-6 and HIV-RNA load (Table 5).

The analysis was therefore extended to ascertain potential associations between serum levels of vIL-6 and factors relevant to HIV disease to the entire HIV-positive group where serum vIL-6 had been measured. This analysis (Table 6) included all 64 HIV-positive patients with (n=34) or without (n=30) KS, where serum vIL-6 was either detected (n=31) or not detected (n=33).

TABLE 6

Characteristics of HIV-positive patients by vIL-6 levels.[a]

| | vIL-6 negative (n = 33) | vIL-6 positive (n = 31) | p value |
|---|---|---|---|
| Sex | | | 0.3474[d] |
| Male | 32 | 28 | |
| Female | 1 | 3 | |
| HIV risk factors | | | 0.6673[d] |
| Homosexual | 31 | 28 | |
| Others | 2 | 3 | |
| Number of KS lesions | | | 0.1321[d] |
| None | 12 | 18 | |
| Any | 21 | 13 | |
| 1-10 | 1 | 1 | 0.297[f] |
| 10-50 | 2 | 4 | |

TABLE 5

Clinical events and laboratory findings in 10 patients with HIV infection

| Case | Sampling MM/YY | KS | vIL-6 (pg/mL) | hIL-6 (pg/mL) | HIV RNA copies/mL | CD4/CD8 cells/μL | antiretroviral therapy NRTIs | NNRTIs | PIs | anti-KS treatment |
|---|---|---|---|---|---|---|---|---|---|---|
| 1 | 12/87 | + | <300 | <1.0 | 60231 | 19/477 | AZT, ddC | — | — | — |
|   | 4/88  | + | 370  | 60.7 | not available | 2/317 | AZT | — | — | Irradiation |
| 2 | 9/93  | + | <300 | 3.8 | <200 | 242/591 | AZT | — | — | — |
|   | 4/99  | + | 5361 | 23.3 | 113846 | 122/514 | ABV | NVP | IDV | VCV, ADM |
|   | 6/99  | + | 7460 | <1.0 | 194258 | 32/255 | ABV | NVP | IDV | VCV, ADM |
| 3 | 6/87  | + | <300 | <1.0 | 33776 | 875/410 | AZT | — | — | — |
|   | 7/87  | + | <300 | <1.0 | 30926 | 972/1458 | AZT | — | — | — |
| 4 | 5/89  | + | <300 | 4.6 | 8376 | 441/2001 | AZT | — | — | — |
|   | 8/89  | + | 470  | 25.0 | 2771 | 502/2279 | — | — | — | — |
| 5 | 3/98  | + | 530  | 6.2 | <200 | 601/1328 | AZT, 3TC | — | NFV | Thalidomide |
|   | 4/99  | + | 714  | 3.7 | <200 | 714/1006 | AZT, 3TC | — | NFV | IL-12 |
|   | 6/99  | + | 671  | 3.8 | <200 | 505/1173 | AZT, 3TC | — | NFV | IL-12 |
| 6 | 8/98  | + | <300 | 65.9 | <200 | 275/1132 | D4T, 3TC | — | IDV | — |
|   | 4/99  | + | <300 | <1.0 | <200 | 287/670 | D4T, 3TC | — | IDV | Thalidomide |
|   | 5/99  | + | <300 | 7.6 | <200 | 345/782 | D4T, 3TC | — | IDV | ADM |
| 7 | 4/99  | + | <300 | <1.0 | <200 | 144/883 | D4T, 3TC | — | NFV | — |
|   | 6/99  | + | <300 | 3.8 | <200 | 137/906 | D4T, 3TC | — | NFV | ADM |
| 8 | 4/99  | + | 4507 | <1.0 | 10176 | 260/398 | AZT, 3TC | — | NFV | CDV |
|   | 6/99  | + | 4753 | <1.0 | 9332 | 325/340 | ABV | NVP | SQV, RTV | ADM |
| 9 | 4/99  | − | 10384 | <1.0 | 130240 | 441/2001 | F-ddA, D4T | — | NFV | — |
|   | 6/99  | − | 11311 | <1.0 | 114598 | 502/2279 | ddI, ABV | — | SQV, RTV | — |
| 10 | 4/99 | − | <300 | <1.0 | 180795 | 28/936 | F-ddA, D4T | — | — | — |
|    | 6/99 | − | <300 | 2.4 | 172227 | 32/1116 | — | — | — | — |

MM/YY: month/year, ABV: abacavir, 3TC: lamivudine; D4T: stavudine; NFV: nelfinavir; SQV: saquinavir; IDV: indinavir; RTV: ritonavir; CDV: cidofovir; VCV: valacyclovir; NVP: nevirapine; ADM: adriamycin TABLE 6-continued Characteristics of HIV-positive patients by vIL-6 levels.[a]

| | vIL-6 negative (n = 33) | vIL-6 positive (n = 31) | p value |
|---|---|---|---|
| >50 | 18 | 8 | |
| KS severity | | | 0.307[f] |
| No KS | 12 | 18 | |
| T0 | 5 | 7 | |
| T1 | 16 | 6 | |
| KS treatment | | | 1.0000[d] |
| None | 17 | 16 | |
| Any | 16 | 15 | |
| anti-herpesvirus agents | 7 | 11 | 0.2691[d] |
| others | 15 | 7 | 0.0686[d] |
| Anti-retroviral agents | | | 1.0000[d] |
| None | 7 | 6 | |
| Any | 26 | 25 | |
| NRTI | 26 | 24 | 1.0000[d] |

TABLE 6-continued

Characteristics of HIV-positive patients by vIL-6 levels.[a]

|  | vIL-6 negative (n = 33) | vIL-6 positive (n = 31) | p value |
|---|---|---|---|
| NNRTI | 2 | 3 | 0.6673[d] |
| PI | 9 | 11 | 0.5919[d] |
| Lymphocyte counts |  |  |  |
| CD4+ T cells (/μL) | 155 ± 181 | 181 ± 190 | 0.3825[e] |
| CD8+ T cells (/μL) | 614 ± 312 | 703 ± 467 | 0.7168[e] |
| CD4/8 ratio | 0.25 ± 0.38 | 0.23 ± 0.18 | 0.2677[e] |
| HIV RNA (copies/mL) | 47329 ± 110189[b] | 49261 ± 99280[c] | 0.9471[e] |
| Lymphadenopathy | 7 | 2 | 0.1498[d] |
| Platelet counts (/μL) | 195 ± 80 | 202 ± 63 | 0.2538[e] |

[a]All participants were enrolled in clinical studies at National Cancer Institute, Bethesda, MD.
[b]n = 18
[c]n = 17
[d]Statistical difference in the subgroup was determined by Fisher's exact test.
[e]Statistical difference was determined by Mann-Whitney U test.
[f]v-value by Cramer's test in the subgroup is shown.
NRTI: nucleoside reverse transcriptase inhibitors, NNRTI: non-nucleoside reverse transcriptase inhibitors, PI: protease inhibitor No direct association was noted between vIL-6 levels and KS severity (p=0.1321, Fisher's exact test), HIV RNA load (p=0.9471, Mann-Whitney U test), CD4 cell counts (p=0.3825, Mann-Whitney U test), and lymphadenopathy p=0.1498, Fischer's exact test). These results suggest that in HIV-infected individuals, circulating vIL-6 is not a critical factor in the progression to KS.

KS, a rare malignancy in the general population, is the leading neoplasm in AIDS occurring in approximately 20% of homosexual and bisexual patients. DNA-based and serology-based studies have demonstrated a consistent association of KSHV with both AIDS-related and AIDS-unrelated forms of KS (Antman et al., N Engl J Med 342:1027-38, 2000). This information and other evidence suggest that KSHV is an essential etiologic agent to the development of KS. Earlier studies have shown that the KSHV-encoded cytokine vIL-6, an early lytic viral gene, is only rarely expressed in KS lesions. In the present study, we detected vIL-6 in 16 of 35 (46%) of serum samples from North American patients with AIDS-associated KS. As expected, we found vIL-6 to be rarely detectable in North American blood donors. However, nearly 57% of patients with AIDS without KS, PEL or MCD had detectable vIL-6 in the circulation. Thus, AIDS patients in this study frequently displayed vIL-6 in the circulation regardless of the presence or severity of KS. These results are consistent with previous studies showing that KSHV replicates in only a minority of spindle cells within KS lesions, and further suggest that KSHV frequently replicates and expresses vIL-6 at some site in KSHV-infected AIDS patients.

Example 12

Pharmaceutical Compositions and Modes of Administration

Various delivery systems for administering the specific binding agents for vIL-6 are known, and include e.g., encapsulation in liposomes, microparticles, microcapsules, expression by recombinant cells, receptor-mediated endocytosis (see, e.g., Wu and Wu, J. Biol. Chem. 62:4429-32, 1987), construction of a therapeutic nucleic acid as part of a retroviral or other vector, etc. Methods of introduction include but are not limited to intradermal, intramuscular, intraperitoneal, intrapleural, intravenous, subcutaneous, intranasal, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, the pharmaceutical compositions may be introduced into the central nervous system by any suitable route, including intraventricular and intrathecal injection; intraventricular injection may be facilitated by an intraventricular catheter, for example, attached to a reservoir, such as an Ommaya reservoir.

In a specific embodiment, it may be desirable to administer the pharmaceutical compositions of the invention locally to the area in need of treatment, for example, by local infusion during surgery, topical application, e.g., in conjunction with a wound dressing after surgery, by injection, through a catheter, by a suppository or an implant, such as a porous, non-porous, or gelatinous material, including membranes, such as silastic membranes, or fibers. In one embodiment, administration can be by direct injection at the site (or former site) of a malignant tumor or neoplastic or pre-neoplastic tissue, such as a Kaposi's sarcoma lesion. In a specific embodiment, administration is performed directly into a vIL-6-expressing cell.

The use of liposomes as a delivery vehicle is one delivery method of interest. The liposomes fuse with the target site and deliver the contents of the lumen intracellularly. The liposomes are maintained in contact with the target cells for a sufficient time for fusion to occur, using various means to maintain contact, such as isolation and binding agents. Liposomes may be prepared with purified proteins or peptides that mediate fusion of membranes, such as Sendai virus or influenza virus. The lipids may be any useful combination of known liposome forming lipids, including cationic lipids, such as phosphatidylcholine. Other potential lipids include neutral lipids, such as cholesterol, phosphatidyl serine, phosphatidyl glycerol, and the like. For preparing the liposomes, the procedure described by Kato et al. (J. Biol. Chem. 266:3361, 1991) maybe used.

In an embodiment where the therapeutic molecule is an antibody, specifically a mAb, combined with a differentiation-inducing agent, administration may be achieved by direct injection, or by use of microparticle bombardment (e.g., a gene gun; Biolistic, Dupont), or coating with lipids or cell-surface receptors or transfecting agents.

The present invention also provides pharmaceutical compositions which include a therapeutically effective amount of the inducing agent with an mAb that neutralizes a biological function of vIL-6, and a pharmaceutically acceptable carrier or excipient. Such carriers include, but are not limited to, saline, buffered saline, dextrose, water, glycerol, ethanol, and combinations thereof. The carrier and composition can be sterile, and the formulation suits the mode of administration. The composition can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, and magnesium carbonate.

In a particular embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule, indicating the quantity of active agent. Where the composition is to be administered by infusion, it can be dispensed with an infusion bottle containing sterile pharmaceutical grade water or saline.

The compositions can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, and procaine. The amount of the inducing agent and disrupting agent that will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

Suppositories generally contain active ingredient in the range of 0.5% to 10% by weight; oral formulations preferably contain 10% to 95% of the active ingredients. The invention also provides a pharmaceutical pack or kit comprising one or more containers filled with one or more of the ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use or sale for human administration.

The pharmaceutical compositions or methods of treatment may be administered in combination with other therapeutic treatments, such as other anti-neoplastic anti-inflammatory, anti-viral or other therapies.

In view of the many possible embodiments to which the principles of our invention may be applied, it should be recognized that the illustrated embodiment is only a preferred example of the invention and should not be taken as a limitation on the scope of the invention. Rather, the scope of the invention is defined by the following claims. We therefore claim as our invention all that comes within the scope and spirit of these claims.

We claim:

1. An isolated functional fragment of a monoclonal antibody or a humanized form thereof, wherein the monoclonal antibody specifically binds Kaposi's sarcoma-associated herpesvirus (KSHV) interleukin-6 (vIL-6), wherein the monoclonal antibody is produced by a hybridoma deposited as American Type Culture Collection (ATCC) Deposit No. PTA-2217, PTA-2218, PTA-2219, or PTA-2220.

2. The isolated functional fragment of claim 1, wherein the monoclonal antibody is a humanized form of the hybridoma deposited as American Type Culture Collection (ATCC) Deposit No. PTA-2217, PTA-2218, PTA-2219, or PTA-2220.

3. The isolated functional fragment of claim 1, wherein the functional fragment is labeled.

4. The isolated functional fragment of claim 3, wherein the label is a radiolabel, a fluorescent label, a colorimetric label, or a luminescent label.

5. The isolated functional fragment of claim 2, wherein the functional fragment is a Fab, Fab', $(Fab')_2$, Fv or a single chain fragment.

6. A method for diagnosing or determining the prognosis of an infection of a subject with a Kaposi's sarcoma-associated herpesvirus (KSHV), comprising
   contacting a sample from the subject with the isolated functional fragment of claim 1, and
   detecting the binding of the monoclonal antibody with the sample,
   wherein binding of the monoclonal antibody to the sample is indicative of the diagnosis or prognosis of the infection of the subject with KSHV.

7. The method of claim 6 wherein the subject has a Kaposi's sarcoma-associated herpes virus (KSHV) associated disorder.

8. The method of claim 6 wherein the disorder is primary effusion lymphoma, Castleman's disease, or Kaposi's sarcoma.

9. The method of claim 6, wherein the monoclonal antibody is labeled.

10. A method of detecting Kaposi's sarcoma-associated herpesvirus (KSHV) interleukin-6 (vIL-6) in a biological sample, comprising
    contacting the biological sample with the functional fragment of the monoclonal antibody of claim 1; and
    detecting binding of the functional fragment of the monoclonal antibody to KSHV vIL-6;
    thereby detecting the presence of KSHV vIL-6 in the sample.

11. The method of claim 10, wherein the functional fragment of the monoclonal antibody is labeled.

12. The method of claim 11, wherein the label is an enzyme, a radioisotope, a fluorescent compound, a colloidal metal, a chemiluminescent compound, a phosphorescent compound, or a bioluminescent compound.

* * * * *

SEQUENCE LISTING

<160> NUMBER OF SEQ ID NOS: 10

<210> SEQ ID NO 1
<211> LENGTH: 13
<212> TYPE: PRT
<213> ORGANISM: Homo sapiens

<400> SEQUENCE: 1

Asp Gly Cys Phe Gln Ser Gly Phe Asn Glu Glu Thr Cys
1               5                   10

<210> SEQ ID NO 2
<211> LENGTH: 6
<212> TYPE: PRT
<213> ORGANISM: Homo sapiens

<400> SEQUENCE: 2

Phe Asn Glu Glu Thr Cys
1               5

<210> SEQ ID NO 3
<211> LENGTH: 13
<212> TYPE: PRT
<213> ORGANISM: Kaposi's sarcoma-associated herpesvirus

<400> SEQUENCE: 3

Asp His Cys Gly Leu Ile Gly Phe Asn Glu Thr Ser Cys
1               5                   10

<210> SEQ ID NO 4
<211> LENGTH: 6
<212> TYPE: PRT
<213> ORGANISM: Kaposi's sarcoma-associated herpesvirus

```
<400> SEQUENCE: 4

Phe Asn Glu Thr Ser Cys
1               5

<210> SEQ ID NO 5
<211> LENGTH: 24
<212> TYPE: DNA
<213> ORGANISM: Artificial Sequence
<220> FEATURE:
<223> OTHER INFORMATION: Mutagenesis oligonucleotide

<400> SEQUENCE: 5
atttagatct tcaattggat gcta                                          24

<210> SEQ ID NO 6
<211> LENGTH: 24
<212> TYPE: DNA
<213> ORGANISM: Artificial Sequence
<220> FEATURE:
<223> OTHER INFORMATION: Mutagenesis oligonucleotide

<400> SEQUENCE: 6
acttagatct gcgggttaat agga                                          24

<210> SEQ ID NO 7
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 7
actggatccc ttaaaaagct cgccgat                                       27

<210> SEQ ID NO 8
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 8
tttggatcct taacgacgga gtttgga                                       27

<210> SEQ ID NO 9
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 9
acgggatcca gtccacccaa atttgac                                       27

<210> SEQ ID NO 10
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 10
cccaagctta ttacttatcg tggacgt                                       27
```